US010472400B2

(12) United States Patent
Rao et al.

(10) Patent No.: US 10,472,400 B2
(45) Date of Patent: Nov. 12, 2019

(54) CARDIAC TROPONIN I ULTRA-SENSITIVE DETECTION REAGENT KIT, AND ULTRA-SENSITIVE DETECTION METHOD THEREFOR

(71) Applicant: SHENZHEN NEW INDUSTRIES BIOMEDICAL ENGINEERING CO., LTD, Shenzhen (CN)

(72) Inventors: Wei Rao, Shenzhen (CN); Jinyun Yuan, Shenzhen (CN); Qin Li, Shenzhen (CN); Sheng Wang, Shenzhen (CN); Hong Xu, Shenzhen (CN); Wu Li, Shenzhen (CN); Tinghua Li, Shenzhen (CN); Jinqiu Fu, Shenzhen (CN)

(73) Assignee: SHENZHEN NEW INDUSTRIES BIOMEDICAL ENGINEERING CO., LTD, Shenzhen (CN)

( * ) Notice: Subject to any disclaimer, the term of this patent is extended or adjusted under 35 U.S.C. 154(b) by 453 days.

(21) Appl. No.: 15/507,630

(22) PCT Filed: Feb. 10, 2015

(86) PCT No.: PCT/CN2015/072675
§ 371 (c)(1),
(2) Date: Feb. 28, 2017

(87) PCT Pub. No.: WO2016/127318
PCT Pub. Date: Aug. 18, 2016

(65) Prior Publication Data
US 2017/0305983 A1 Oct. 26, 2017

(51) Int. Cl.
| C07K 14/47 | (2006.01) |
| C09K 11/06 | (2006.01) |
| G01N 21/76 | (2006.01) |
| G01N 33/566 | (2006.01) |
| G01N 33/68 | (2006.01) |
| A61K 39/00 | (2006.01) |
| C07D 237/32 | (2006.01) |
| C07D 401/14 | (2006.01) |

(52) U.S. Cl.
CPC .......... *C07K 14/4716* (2013.01); *C09K 11/06* (2013.01); *G01N 21/76* (2013.01); *G01N 33/566* (2013.01); *G01N 33/6887* (2013.01); *A61K 2039/6056* (2013.01); *C07C 2603/74* (2017.05); *C07D 237/32* (2013.01); *C07D 401/14* (2013.01)

(58) Field of Classification Search
None
See application file for complete search history.

(56) References Cited

U.S. PATENT DOCUMENTS

| 5,616,460 A * | 4/1997 | Figard ............... G01N 33/5306 435/5 |
| 7,285,418 B2 | 10/2007 | Katrukha et al. |
| 10,114,030 B2 | 10/2018 | Rao et al. |
| 2011/0129818 A1 | 6/2011 | Adamczyk et al. |
| 2017/0363627 A1 | 12/2017 | Rao et al. |
| 2018/0231540 A1 | 8/2018 | Rao et al. |
| 2018/0299436 A1 | 10/2018 | Rao |

FOREIGN PATENT DOCUMENTS

| CN | 1644685 A | 7/2005 |
| CN | 1888901 A | 1/2007 |
| CN | 101029897 A | 9/2007 |
| CN | 101226200 A | 7/2008 |
| CN | 102192986 A | 9/2011 |
| CN | 102257391 A | 11/2011 |
| CN | 102426246 A | 4/2012 |
| CN | 102901832 A | 1/2013 |
| CN | 103940986 A | 7/2014 |
| EP | 2679997 A1 | 1/2014 |

OTHER PUBLICATIONS

Extended European Search Report for Application No. 15881480.6, dated Jun. 18, 2018, (8 pages).
Tsaloglou et al., "A fluorogenic heterogeneous immunoassay for cardiac muscle troponin cTnI on a digital microfluidic device", Jul. 30, 2014, (10 pages).
English Translation of International Search Report for International Application No. PCT/CN2015/072675, dated Nov. 17, 2015, (3 pages).
"Hytest Product Catalogue 2012-2013", Dec. 31, 2013, (60 pages).

* cited by examiner

*Primary Examiner* — Christine Foster
*Assistant Examiner* — Ellen J Marcsisin
(74) *Attorney, Agent, or Firm* — Kagan Binder, PLLC

(57) ABSTRACT

A cardiac troponin I ultra-sensitive detection reagent kit, a preparation method, and a detection method. The reagent kit comprises at least one first anti-cardiac troponin I antibody marked with a trace marker and at least one second anti-cardiac troponin I antibody coated on magnetic microspheres, the first anti-cardiac troponin I antibody and cardiac troponin I binding site being different from the second anti-cardiac troponin I antibody and cardiac troponin I binding site. The reagent kit may further comprise a diluent capable of significantly reducing non-specific binding in a detection process, so as to further increase the detection accuracy and sensitivity. The method using the reagent kit to detect cardiac troponin I sensitively and accurately detects the amount of cardiac troponin I in a sample, and provides more timely and reliable information for the early diagnosis and treatment of AMI.

15 Claims, 2 Drawing Sheets

CARDIAC TROPONIN I ULTRA-SENSITIVE DETECTION REAGENT KIT, AND ULTRA-SENSITIVE DETECTION METHOD THEREFOR

TECHNICAL FIELD

The present disclosure relates to the field of detection of biochemical substances, in particular to an ultrasensitive cardiac troponin I assay kit and its preparation method, as well as a cardiac Troponin I ultra-sensitive assay methods.

BACKGROUND

Troponin is a regulatory protein for contraction of the striated muscle, present in myocardium and skeletal muscle, and consists of three subunits, i.e., TnI, TnC, and TnT. The three subunits form a complex that plays an important regulatory role in muscle contraction and relaxation. TnI is an inhibitory subunit of actin, which has three subtypes: fast skeletal subtype (fTnI), slow skeletal muscle subtype (sTnI), and cardiac subtype (cardiac troponin I, cTnI). The cTnI has a molecular mass of 23.9 kD, with 210 amino acid residues. Increased levels of cTnI may be an important serological marker for diagnosis of acute myocardial infarction (AMI). When acute myocardial infarction occurs, cTnI is released into the bloodstream within 4-8 hours due to myocardial obstruction, so that its concentration is beyond the concentration range for a healthy person. In general, cTnI concentrations are highest in 12-18 hours following onset of AMI and remain for 5 to 10 days.

Acute myocardial infarction is myocardial necrosis caused by acute and persistent ischemia and hypoxia of coronary artery. Severe and persistent posterior sternal pain is common clinically, which cannot be completely relieved by rest and nitrate drugs, and accompanied by increased levels of serum myocardial enzymes and progressive ECG changes, which can be further complicated by arrhythmia, shock, or heart failure, and even life-threatening. It is one of the common cardiology diseases, which seriously endangers human health. This disease is most common in Europe and the United States. In the United States each year about 1.5 million people have an onset of myocardial infarction. In recent years, China showed a clear upward trend, with the number of new cases every year being at least 0.5 million and at least 2 million patients currently suffering. In recent years, great progress has been made in treating AMI, changing from passive conservative treatment to positive elimination of thrombosis or percutaneous coronary artery dilatation, and even coronary artery bypass surgery. This set a high standard for early accurate diagnosis of AMI, while the AMI attack sensitivity is only about 50%. The sensitivity gradually increases with time to be 90% or more at 6 h, showing a tendency of increasing sensitivity over time, which means that the key issue in early accurate diagnosis of AMI is to increase the sensitivity of the assay method.

At present, AMI assay methods mainly include characteristic ECG changes and dynamic changes of serum biomarker. However, about 25% of myocardial infarction patients have no typical clinical symptoms during the early stage of the disease, about 50% of AMI patients lack ECG-specific changes. With ECG changes and clinical symptoms alone, AMI diagnostic accuracy was merely 75%. In this case, the detection of myocardial injury markers is particularly important in the diagnosis of AMI. Myocardial injury markers are mainly creatine kinase isoenzyme (CK-MB) and cTnI. Since CTnI has the advantages of rapid dynamic release, complete curve, distinct peak, strong tissue specificity, long diagnosis window period, rapid assay process, and early appearing in blood after myocardial injury, the AMI diagnostic method based on cTnI is preferred over the AMI diagnostic method based on CK-MB, and has been widely accepted clinically. CTnI has not only become the "gold standard" for diagnosis of acute myocardial infarction, but also has become the most suitable marker for monitoring, clinical observation, risk classification, and prognosis evaluation of myocardial disease.

There are many ways of cTnI determination, mainly including radioisotope immunoassay (RIA), enzyme-linked immunosorbant assay (ELISA), and colloidal gold immunochromatography (ICA), and so on. In recent years, with the development of cTnI research, some new and more accurate assay methods were developed in the clinical laboratory, such as chemiluminescence (CLIA).

Radioisotope immunoassay has many problems, such as complicated operation, long testing time, unsuitablility for large-batch assay, poor reproducibility, and radionuclide contamination.

The mechanism for Enzyme-linked immunosorbant assay is using a specific antibody coated with a solid-phase carrier as the first antibody, adding serum to be tested, then add a biotinylated second antibody to form a double sandwich, washing for separation after incubation, and adding a luminescent matrix substrate. The concentration of cTnI was obtained by comparing the measured luminous intensity of the matrix with the standard curve. However, the enzyme-linked immunosorbant assay has many disadvantages such as complicated operation, long measurement period, relatively low sensitivity, narrow linear range, and especially the low content of serum cTnI, the detection of cTnL by ELISA method showed obviously poor sensitivity, which makes it impossible to quickly diagnose the onset of acute myocardial infarction (AMI) in the early stage, limiting further application of ELISA in the clinical detection of cTnI.

Colloidal gold immunochromatography uses less sample and is simple and fast, suitable for cTnI bedside detection. The basic mechanism is to detect cTnI by use of the binding of two anti-cTnI monoclonal antibodies. When the serum sample is dropped into the absorption hole, a first gold-labeled antibody and cTnI bind to form an antibody-antigen complex, and a second immobilized cTnI monoclonal antibody captures this complex, generating a pink band, while there is no band present in the reaction loop in case of absence of the complex. However, colloidal gold immunochromatography can only apply for qualitative determination and is of poor sensitivity for quantitative determination. Test cards developed based colloidal gold immunochromatography, though capable of rapid qualitative detection of cTnI, also has the problem of the low sensitivity. Early in AMI, when the serum contains only a small amount of cTnI, colloidal gold immunochromatography cannot provide accurate diagnosis of AMI onset, and thus its clinical application is still greatly restricted.

Chemiluminescence (CL) is a type of labeled immunoassay technique for detecting trace antigen or antibody by combining luminescence analysis and immunological reaction, which comprises two parts, i.e., immunological reaction system and chemiluminescence analysis system. Chemiluminescence analysis system uses chemiluminescent substances to form an intermediate of an excited state via catalysis by a catalyst and oxidation by an oxidant. When the excited intermediate goes back to a stable ground state, it will emit photons at the same time; the quantum yield of light is measured with the use of luminescence signal measuring instrument. The immune response system will mark the marker material directly on the antigen or antibody, form antigen—antibody complex by a specific reaction, and then detect by a detection method of the corresponding marker. CLIA's main advantages are its high sensitivity, wide linear range, long marker lifetime, no radioactive hazards, and potential for full automation.

The cTnI kit supplied by Siemens includes a ReadyPack® Master Kit containing the ADVIA Centaur® High Sensitivity TnI™ Double Labeling Reagent, solid phase reagents, and adjuvant reagents. The double labeling reagents consist of acridinine-labeled goat polyclonal anti-cTnI antibody (~0.15 μg/mL) and two biotin-labeled mouse monoclonal anti-cTnI antibody (~2.0 μg/mL). The solid phase reagent is a latex magnetic particle suspension. The adjuvant reagent is a non-magnetic latex particle. The ADVIA Centaur Ultrasensitive TnI assay of this manufacture is a 3-point sandwich immunoassay using direct chemiluminescence technique. During the assay, the antibody in the double labeling reagent binds to troponin I in the sample, producing an immune complex. The biotin contained in the immune complexe randomly binds to labeled streptavidin on the magnetic particles.

Roche provides a cTnI assay kit, which can bind with the antigen with biotinylated anti-cTnI monoclonal antibody and ruthenium (Ru) complex-labeled anti-cTnI monoclonal antibody to form a sandwich structure, and detect cTnI by electrochemically luminescence Immunoassay (ECLIA).

Chemiluminescence method has the advantages of accuracy, strong specificity, and good precision, while its sensitivity is much higher than that of enzyme-linked immunosorbant assay and colloidal gold immunochromatography. However, the sensitivity of existing cTnI commercial test kit for clinical applications is still not high enough, with an analytical sensitivity of 5 pg/mL or above, and thus cannot accurately detect ultra-low concentrations of cTnI or meet the high standards of early diagnosis of AMI.

SUMMARY OF THE INVENTION

In view of the drawbacks of the prior art, it is an object of the present disclosure to provide a cTnI assay kit and a method for preparing the same. The kit has ultra-high sensitivity and can provide accurate assay results for early diagnosis of AMI, thereby improving the sensitivity of early diagnosis of AMI.

The present disclosure also provides a method for detecting cTnI, with high sensitivity for early diagnosis of AMI, and provides a more advanced method thereof.

The present disclosures provides a cTnI assay kit, comprising at least one first anti-cTnI antibody labeled with a trace marker and at least one second anti-cTnI antibody coated on a magnetic microsphere, wherein a binding site of the first anti-cTnI antibody to cTnI is different from a binding site of the second anti-cTnI antibody to cTnI. The first anti-cTnI antibody and the second anti-cTnI antibody may be anti-cTnI monoclonal antibodies and/or anti-cTnI polyclonal antibodies. The kit is a ultrasensitive assay kit, with high sensitivity when used in the detection of cTnI.

In the present disclosure, the first anti-cTnI antibody and the second anti-cTnI antibody differ in their binding sites to cTnI. Accordingly, in an equivalent aspect of the present disclosure, the kit may also include at least one second anti-cTnI antibody labeled with a trace marker and at least one first anti-cTnI antibody coated on magnetic microspheres. For the purposes of the present disclosure, hypersensitivity refers to detection sensitivity below 5 pg/mL, in particular below 3 pg/mL.

The present disclosure adopts the double antibody sandwich method to detect cTnI. This method adopts two or more anti-cTnI monoclonal or polyclonal antibodies, wherein the one or more labeled anti-cTnI monoclonal or polyclonal antibodies are used to capture a cTnI amino acid segment, while other anti-cTnI monoclonal or polyclonal antibodies that are linked to the vector are used to bind the amino acid segments of cTnI that are different from the ones binded by the former.

Preferably, the binding site where the first anti-cTnI antibody binds to cTnI is a 10-100 amino acid segment of cTnI; the binding site where the second anti-cTnI antibody binds to cTnI is a 40-200 amino acid segment of cTnI. Selection of cTnI antibodies that bind with these segments may facilitate better labeling of the cTnI antibody or better coating of the magnetic microspheres, favoring the binding of cTnI antibody to cTnI during the assay, and improve the detection specificity and accuracy.

In a preferred embodiment, the kit may comprise two types of the first anti-cTnI antibodies, the binding sites of which to cTnI being a 10-50 amino acid segment and a 60-100 amino acid segment of the cTnI, respectively, and wherein the kit may further comprise two types of the second anti-cTnI antibodies, the binding sites of which to cTnI being a 40-80 amino acid segment and a 120-200 amino acid segment of cTnI, respectively.

According to the present disclosure, the trace marker can be selected from the group consisting of trace markers commonly used in the art for labeling antigens or antibodies, such as adamantane, luminol, isoluminol and its derivatives, acridinium esters, alkaline phosphatase, or horseradish peroxidase, and especially preferred as N-(4-aminobutyl)-N-ethylisoluminol (ABEI).

Magnetic microspheres suitable for use in the present disclosure are also known as magnetic beads and may be magnetic microspheres commonly used in the art. Preferably, the magnetic microspheres used in the present disclosure are prepared by combining nano-sized $Fe_2O_3$ or $Fe_3O_4$ magnetic particles and an organic polymeric material to form micro-sized solid-phase microspheres with superparamagnetism and extremely large protein adsorption capacity, which can be quickly magnetized in a, external magnetic field and has zero residual magnetism after withdrawal of the magnetic field. The type of the organic polymeric material is not particularly limited, and may be selected as needed.

The magnetic microspheres used in the present disclosure should meet the requirements of 0.1-5 μm in diameter. The magnetic microspheres can also be surface modified to carry a variety of active functional groups, including but not limited to —OH, —COOH, —$NH_2$.

In a particular embodiment, the magnetic microsphere is a complex of $Fe_2O_3$ or $Fe_3O_4$ magnetic nanoparticles with an organic polymeric material, with a particle diameter of 0.1 to 5 μm; and wherein the magnetic microsphere is optionally modified by surface modification to carry one or more active functional groups.

According to the present disclosure, each of the first anti-cTnI antibody and the second anti-cTnI antibody in the kit may have a concentration of 1-20 μg/mL, the trace marker may have a concentration of 5-500 ng/mL, and the magnetic microsphere may have a concentration of 0.1-2 mg/mL. The concentration of each component above is based on the amount of components of the kit containing the component.

According to the present disclosure, the trace marker directly or indirectly labels the first anti-cTnI antibody, and the indirect labeling comprises indirect labeling either by a system of fluorescein isothiocyanate (FITC) and anti-isothiocyanate fluorescein antibody or by a system of streptavidin CSA) and biotin. Direct labeling means that ABET is directly connected to the first anti-cTnI antibody for labeling. Indirect labeling refers to the use of an intermediary linking system to obtain the first anti-cTnI antibody labeled with ABEI, the intermediary linking system including, but are not limited to, FITC and anti-FITC antibody system, or streptavidin and biotin systems. The present inventors have found that indirect labeling facilitates attenuation of spatial effects and signal amplification, which makes the detection more sensitive.

According to the present disclosure, the second anti-cTnI antibody directly or indirectly coats the magnetic microspheres, and the indirect coating of the magnetic microspheres comprises indirect coating either by a system of fluorescein isothiocyanate and anti-isothiocyanate fluorescein antibody or by a system of streptavidin and biotin. Direct coating means that magnetic microspheres are directly coated by the second anti-cTnI antibody. Indirect coating refers to the use of an intermediary linking system to coat the magnetic microspheres with the second anti-cTnI antibody, the intermediary linking system including, but are not limited to, FITC and anti-FITC antibody system, or streptavidin and biotin systems. Indirect coating is advantageous in facilitating attenuation of spatial effects and signal amplification, which makes the detection more sensitive.

According to some embodiments of the present disclosure, the kit comprises any one selected from the group consisting of A1 to A3 and any one selected from the group consisting of B1 to B3, wherein A1 is a solution of the first anti-cardiac troponin I antibody labeled (that is, direct labeling) with a trace marker; A2 is a streptavidin solution labeled (that is, direct labeling) with a trace marker and a solution of the first anti-cardiac troponin I antibody that is biotinylated; A3 is a solution of the anti-isothiocyanate fluorescein antibody labeled (that is, direct labeling) with a trace marker and a solution of the first anti-cardiac troponin I antibody labeled with fluorescein isothiocyanate. B1 is a second anti-cardiac troponin I antibody solution coated (that is, direct coating) on the magnetic microspheres; B2 is a streptavidin solution coated (that is, direct coating) on the magnetic microspheres and a solution of the biotinylated second anti-cardiac troponin I antibody; B3 is a solution of the anti-isothiocyanate fluorescein antibody coated (that is, direct coating) on the magnetic microspheres and a second anti-cardiac troponin I antibody solution labeled with fluorescein isothiocyanate; and each solution of the components A1-A3 and the components B1-B3 optionally comprises bovine serum albumin (BSA) and/or a preservative, respectively. The concentration of BSA is preferably 0.01-5 g/mL.

The present disclosure further provides a diluent, wherein the diluent comprises the following components: bovine serum albumin, neonatal bovine serum, goat serum, horse serum, dithiothreitol, tris (hydroxymethyl) aminomethane, hydrated 2-morpholinoethanesulfonic acid (e.g., 2-morpholinoethanesulfonic acid monohydrate), ethylene glycol, glycerol, Tween-80, casein, and disodium ethylenediaminetetraacetate.

In a preferred embodiment of the present disclosure, the components of the diluent are present in the following concentrations: 1 to 10 g/L of the bovine serum albumin, 1 to 50 v/v % of the fresh bovine serum, 0.1 to 10 v/v % of the goat serum, 0.1 to 10 v/v % of the horse serum, 1 to 100 mmol/L of the dithiothreitol, 1 to 100 mmol/L of the trimethylolaminomethane, 1 to 100 mmol/L of the hydrated 2-morpholinoethanesulfonic acid, 0.1 to 10 v/v % of the ethylene glycol, 0.1 to 10 v/v % of the glycerol, 0.01 to 2 v/v % of the Tween-80, 0.1 to 10 g/L of the casein, and 0.1 to 10 g/L disodium ethylenediaminetetraacetate.

The diluent preferably uses water as a solvent. The diluent also preferably further comprises 0.01 to 1 g/L of a preservative.

Preservatives suitable for use in the present disclosure may be selected from preservatives commonly used in the art, such as any one or a mixture of any two or more selected from the group consisted of potassium sorbate, sodium benzoate, sodium azide, sodium nitrite, Proclin 300 (one of the most commonly used preservatives for immunodiagnostics, the major active ingredients being 2-methyl-4-isothiazolin-3-ketone and 5-chloro-2-methyl-4-isothiazolin-3-ketone) and antibiotics.

In a preferred embodiment of the present disclosure, the kit provided by the present disclosure further comprises a diluent as described above. The diluent can be added during the detection process, and the diluent can eliminate various factors interfering immune response, such as rheumatoid factor (RF), human anti-mouse antibody (HAMA), heterophilic antibody, and antinuclear antibody (ANA), to provide a more favorable conditions for reaction between antibody and antigen. Thus, addition of the diluent can significantly reduce non-specific binding of sample detection, thereby further improving the reaction sensitivity and detection accuracy.

In accordance with the present disclosure, the kit further comprises a low point calibrator and a high point calibrator for cTnI and optionally a buffer. The low point calibrator and the high point calibrator of the present disclosure are relative to each other, wherein "low point calibrator" refers to a calibrator obtained by diluting cTnI with a 50% bovine serum preparation to a concentration of 0.01 to 2206 ng/mL; and "high point calibrator" refers to a calibrator obtained by diluting cTnI with a 50% bovine serum preparation at a concentration of 17668-50000 ng/mL. The low and high point calibrators optionally contain BSA and/or preservatives at a concentration of 0.01 to 5 g/mL, respectively.

In a specific embodiment of the disclosure, the kit comprises the following components: a) cTnI antibody-labeled ABEI, cTnI antibody concentration being 50 ng/mL to 5000 ng/mL and ABEI concentration being 5 ng/mL to 500 ng/mL; b) magnetic microspheres coated with a cTnI antibody, cTnI antibody concentration being 1-20 μg/mL and the magnetic microsphere concentration being 0.1 mg/mL to 2 mg/mL; c) a low point calibrator at a concentration of 0.01 to 2206 pg/mL; d) a high point calibrator at a concentration of 17668-50000 pg/mL; e) BSA with a concentration of 0.01-5 g/mL; f) a preservative; and g) a diluent as described above.

In a specific embodiment of the disclosure, the kit comprises the following components: a) cTnI antibody-labeled ABEI, cTnI antibody concentration being 50 ng/mL to 5000 ng/mL and ABEI concentration being 5 ng/mL to 500 ng/mL; b) FITC-labeled cTnI antibodycTnI antibody concentration being 50 ng/mL to 5000 ng/mL and FITC concentration being 5 ng/mL to 500 ng/mL; c) magnetic microspheres coated with FITC monoclonal or polyclonal antibodies, the FITC monoclonal or polyclonal antibody concentrations being 1-20 µg/mL and the magnetic microsphere concentration being 0.1 mg/mL to 2 mg/mL; d) a low point calibrator at a concentration of 0.01 to 2206 pg/mL; e) a high point calibrator at a concentration of 17668 to 50000 pg/mL; f) BSA at a concentration of 0.01-5 g/mL; g) a preservative; and h) a diluent as described above.

In a specific embodiment of the disclosure, the kit comprises the following components: a) cTnI antibody-labeled ABEI, cTnI antibody concentration being 50 ng/mL to 5000 ng/mL and ABEI concentration being 5 ng/mL to 500 ng/mL; b) a biotinylated cTnI antibody having a cTnI antibody concentration of 50 ng/mL to 5000 ng/mL and a biotin concentration of 5 ng/mL to 500 ng/mL; c) magnetic microspheres coated with streptavidin, the streptavidin concentration being 1-20 µg/mL and the magnetic microsphere concentration being 0.1 mg/mL to 2 mg/mL; d) a low point calibrator at a concentration of 0.01-2206 pg/mL; e) a high point calibrator at a concentration of 17668 to 50000 pg/mL; f) BSA at a concentration of 0.01 to 5 g/mL; g) a preservative; and h) a diluent as described above.

In a specific embodiment of the disclosure, the kit comprises the following components: a) a streptavidin-labeled cTnI antibody having a cTnI antibody concentration of 50 ng/mL to 5000 ng/mL and a streptavidin concentration concentration of 1-20 µg/mL; b) biotin-labeled ABEI, having a biotin concentration of 5 ng/mL to 500 ng/mL and an ABEI concentration of 5 ng/mL to 500 ng/mL; c) magnetic microspheres coated with cTnI antibody, with a cTnI antibody concentration of 1-20 µg/mL and magnetic microsphere concentration of 0.1 mg/mL-2 mg/mL; d) a low point calibrator with a concentration of 0.01-2206 pg/mL; e) a high point calibrator with a concentration of 17668-50000 pg/mL; f) BSA at a concentration of 0.01-5 g/mL; g) a preservative; and h) a diluent as described above.

In a specific embodiment of the disclosure, the kit comprises the following components: a) a cTnI antibody labeled with a FITC monoclonal antibody or a polyclonal antibody, having a cTnI antibody concentration of 50 ng/mL to 5000 ng/mL and a concentration of FITC monoclonal or polyclonal antibody of 1-20 µg/mL; b) a FITC-labeled ABEI, the concentration of FITC being 5 ng/mL to 500 ng/mL and the ABEI concentration being 5 ng/mL to 500 ng/mL; c) magnetic microspheres coated with cTnI antibody, the cTnI antibody concentration being 1-20 µg/mL and the magnetic microsphere concentration being 0.1 mg/mL to 2 mg/mL; d) a low point calibrator with a concentration of 0.01-2206 pg/mL; e) a high point calibrator with a concentration of 17668-50000 pg/mL; f) BSA at a concentration of 0.01-5 g/mL; g) a preservative; and h) a diluent as described above.

In a specific embodiment of the disclosure, the kit comprises the following components: a) a streptavidin-labeled cTnI antibody having a cTnI antibody concentration of 50 ng/mL to 5000 ng/mL and a streptavidin concentration of 1-20 µg/mL; b) a biotin-labeled ABEI with a biotin concentration of 5 ng/mL to 500 ng/mL and an ABET concentration of 5 ng/mL to 500 ng/mL; c) cTnI antibody labeled with FITC, having a cTnI antibody concentration of 50 ng/mL to 5000 ng/mL and a concentration of FITC being 5 ng/mL to 500 ng/mL; d) magnetic microspheres coated with a FITC monoclonal antibody or a polyclonal antibody, the FITC monoclonal antibody or polyclonal antibody having a concentration of 1 to 20 g/mL, the magnetic microspheres having a concentration of 0.1 mg/mL to 2 mg/mL; e) a low point calibrator at a concentration of 0.01 to 2206 pg/mL; f) a high point calibrator at a concentration of 17668 to 50000 pg/mL; /g) BSA at a concentration of 0.01-5 g/mL; h) a preservative; and i) a diluent as described above.

In a specific embodiment of the disclosure, the kit comprises the following components: a) a FITC monoclonal antibody or polyclonal antibody-labeled cTnI antibody, the concentration of cTnI antibody being 50 ng/mL to 5000 ng/mL and the concentration of the FITC monoclonal antibody or polyclonal antibody being 1-20 µg/mL; b) FITC-labeled ABEI, with FITC concentration being 5 ng/mL to 500 ng/mL and ABEI concentration being 5 ng/mL to 500 ng/mL; c) a biotinylated cTnI antibody, cTnI antibody concentration being 50 ng/mL to 5000 ng/mL and biotin concentration being 5 ng/mL to 500 ng/mL; d) magnetic microspheres coated with streptavidin having a streptavidin concentration of 1-20 µg/mL and the magnetic microsphere concentration being 0.1 mg/mL to 2 mg/mL; e) a low point calibrator at a concentration of 0.01 to 2206 pg/mL; f) a high point calibrator at a concentration of 17668 to 50000 pg/mL; g) BSA at a concentration of 0.01-5 g/mL; h) a preservative; i) a diluent as described above.

The present disclosure provides a method for preparing a kit as described above, said method comprising: labeling, directly or indirectly, a trace marker to at least one first anti-cTnI antibody; coating the second anti-cTnI antibody directly or indirectly on magnetic microspheres.

According to the method of the present disclosure, the indirect labeling comprises labeling the anti-CTnI antibody either by a system of fluorescein isothiocyanate and anti-isothiocyanate fluorescein antibody or by a system of streptavidin and biotin.

According to the method of the disclosure, the indirect coating comprises coating the second anti-cTnI antibody on magnetic microspheres either by a system of fluorescein isothiocyanate and anti-isothiocyanate fluorescein antibody or by a system of streptavidin and biotin.

The kit preparation method according to the present disclosure may further comprise the preparation of the diluent as described above provided by the present disclosure, the method comprising mixing the components of the diluent with a solvent homogeneously.

The kit preparation method according to the present disclosure may further comprise the preparation of a low point calibrator and a high point calibrator, and may further comprise an assembly of the kit.

According to the present disclosure, there is also provided a method of detecting cTnI, comprising detecting cTnI concentration in a subject sample using a chemiluminescent immunoassay using a kit as described above.

In a specific embodiment, the cTnI assay method according to the present disclosure may comprise mixing components of a kit comprising a first anti-cardiac troponin I antibody and a second anti-cardiac troponin I antibody with a subject sample, and measuring a light intensity signal of the subject sample, and calculating a concentration of cardiac troponin I in the subject sample by comparing the light intensity signal with that of the calibrator of the cardiac troponin I; wherein each of the first anti-cardiac troponin I antibody and the second anti-cardiac troponin I antibody in the kit has a concentration of 1-20 ng/mL, the trace marker has a concentration of 5-500 ng/mL, and the magnetic microsphere has a concentration of 0.1-2 mg/mL.

According to the present disclosure, the subject sample may be directly obtained serum, plasma, or whole blood, or may be a sample obtained by separation of a human blood sample.

Specifically, the first anti-cTnI antibody and the second anti-cTnI antibody in the kit are allowed to form a diabody sandwich pattern of the first anti-cTnI antibody-cTnI-the second anti-cTnI antibody with cTnI in the subject sample, a luminescent substrate is added, and then the concentration of cTnI is measured by chemiluminescence immunoassay.

A schematic representation of detection using a kit of the present disclosure is illustrated in FIG. 1.

In one embodiment, the method for detecting cTnI concentration comprises detecting cTnI concentration by chemiluminescence immunoassay using a kit as described above. In a preferred embodiment of the present disclosure, the process is carried out fully automatically. According to the present disclosure, the chemiluminescence immunoassay analyzer is preferably a Maglumi series chemiluminescence immunoassay analyzer (manufactured by Shenzhen New Industrial Biomedical Engineering Co., Ltd.).

With the kit provided by the present disclosure, the cTnI concentration can be measured with ultra-high sensitivity, with the detection sensitivity, for example, up to 1 pg/mL and the functional sensitivity up to, for example, 2.5 pg/mL. When used in combination with a chemiluminescence immunoassay analyzer, detection of cTnI concentration results in a sample can be achieved in a fully automatic, fast, sensitive, and quantitative way. The detection sensitivity according to the disclosure can be 5 to 200 times higher than that of the prior art, and thus the cTnI content in the sample can be detected more sensitively, thereby providing more accurate detection result for the early diagnosis of AMI, improving the sensitivity of AMI early diagnosis, so that it is possible to have early and accurate diagnosis of AMI and provide adequate time for the treatment of AMI.

■ —cTnI antigen; ●—magnetic microsphere; ※—other components in the sample; Y -antibodies against cTnI;

—cTnI antibody labeled with ABEI; ※—cTnI antibody coated on magnetic microspheres; —optical signal.

Figure 1:
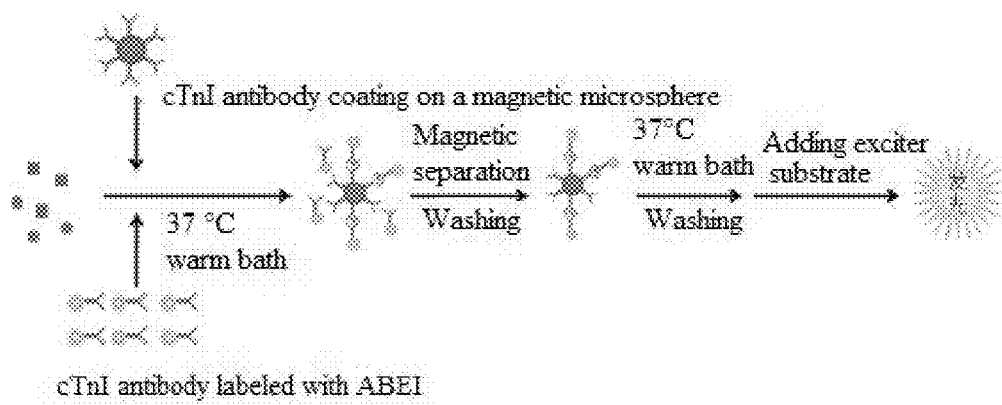
FIG. 1 is a schematic representation of the mechanism of the cTnI assay kit for detecting cTnI in a sample according to the present disclosure; wherein the referential signs in the figures have the following meanings, respectively.
Figure 2:
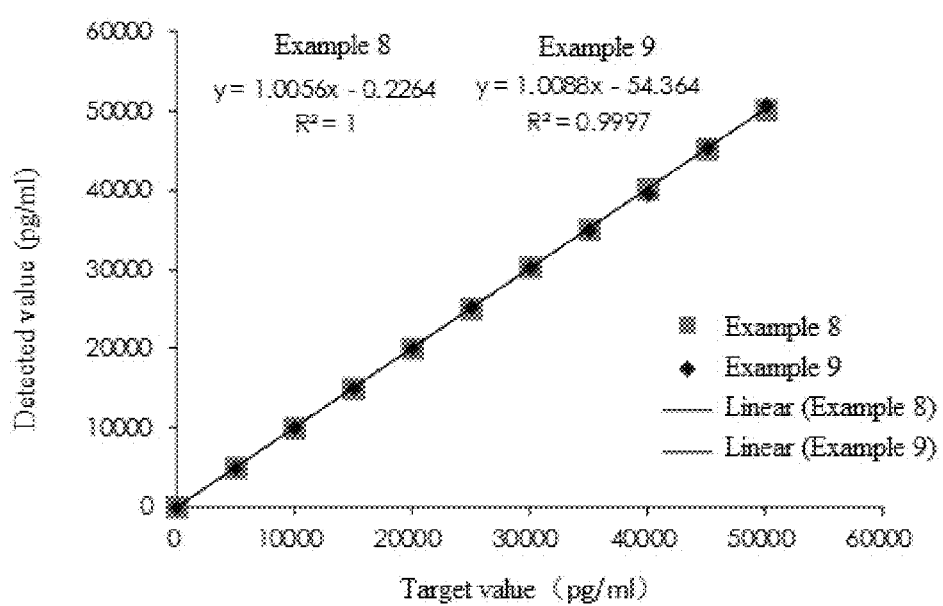

FIG. 2 shows the comparison of the linear test results of Example 8 and Example 9.

Figure 3:
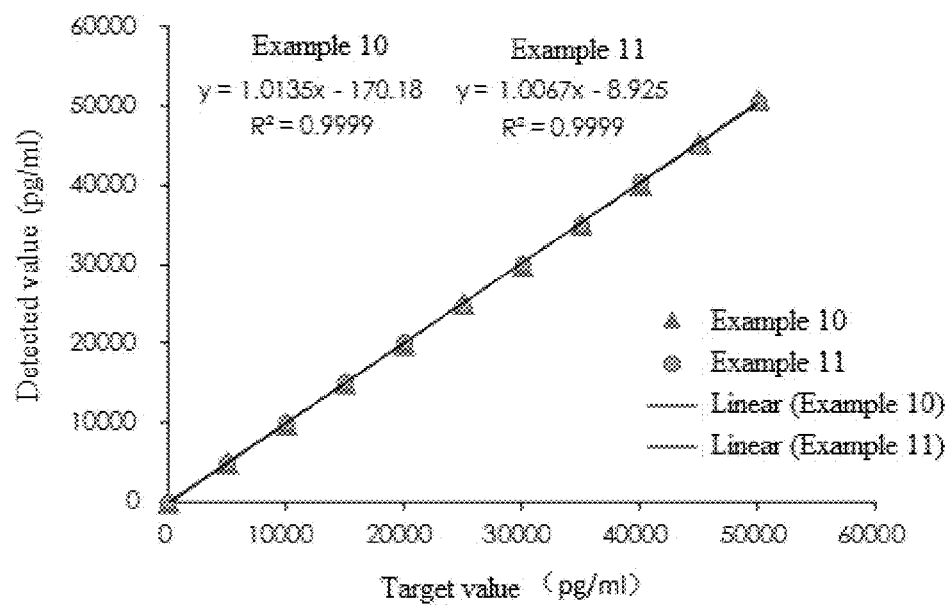

FIG. 3 shows the comparison of the linear test results of Example 10 and Example 11.

DETAILED DESCRIPTION

The present disclosure will be further described below by way of specific examples, and it is to be understood that the scope of the present disclosure is not limited thereto.

Preparation Example 1: Preparing a Suspension of Magnetic Microspheres Coated with cTnI Monoclonal or Polyclonal Antibodies The immunomagnetic microspheres used in this preparative procedure was chosen to be a suspension of nanomagnetic microspheres at a concentration of 100 mg/mL with a hydroxyl group of 95 mg KOH/g, manufactured by Merck.

Preparation of solution A (pH3.6 acetate buffer): 2.55 g of sodium acetate trihydrate was weighed, dissolved in 4500 mL of purified water, combined with 14 mL of acetic acid, mixed well, and added with purified water to a constant volume of 5000 mL (pH 3.6).

The magnetic microspheres were suspended in the above-mentioned pH 3.6 acetate buffer with a volume 5 times of the coating volume so that the concentration of the magnetic microspheres was 20 mg/mL. 1-cyclohexyl-2-morpholino-ethylcarbodiimide P-toluenesulfonate (CMC) was added to a concentration of 10 mg/mL. Purified cTnI monoclonal antibody or polyclonal antibody was added to the resulting solution in a weight ratio of 1 mg:12 µg (resulting solution: cTnI monoclonal or polyclonal antibody), and reacted in a constant temperature shock water bath at 37° C. for 24 hours.

The volume ratio of 0.1 mol/l PBS buffer:purified water=1:9 was used to prepare 500 mL of PBS buffer, pH 7.4. 2.5 g of BSA was added, well mixed, and dissolved, to obtain a microsphere washing solution. The magnetic microspheres after warm were added into a beaker, then placed on a magnet for precipitation, had the supernatant drained, added with 5× microsphere washing solution for stirring and cleaning, then placed on the magnet until the supernatant became clear, and had the supernatant discarded. The washing step was repeated for four times.

Suspension of magnetic microspheres: After washing, the magnetic microspheres were added into a BSA aqueous solution with a coating volume (5 g/L, containing 1 g/L sodium azide) to obtain a suspension of magnetic microspheres with a suspension concentration of 20 mg/mL, the volume of the suspension being the coating volume described in this preparation step.

Preparation Example 2: Preparing a Suspension of Magnetic Microspheres Coated with Streptavidin The immunomagnetic microspheres used in this preparative procedure was chosen to be a suspension of nanomagnetic microspheres at a concentration of 100 mg/mL with a hydroxyl group of 95 mg KOH/g, manufactured by Merck.

Preparation of solution A (pH3.6 acetate buffer): 2.55 g of sodium acetate trihydrate was weighed, dissolved in 4500 mL of purified water, combined with 14 mL of acetic acid, mixed well, and added with purified water to a constant volume of 5000 mL (pH 3.6).

The magnetic microspheres were suspended in the above-mentioned pH 3.6 acetate buffer with a volume equivalent to the coating volume so that the concentration of the magnetic microspheres was 20 mg/mL. CMC was added to a concentration of 10 mg/mL. Streptavidin was added to the resulting solution in a weight ratio of 1 mg:12 µg (resulting solution: streptavidin), and reacted in a constant temperature shock water bath at 37° C. for 24 hours.

Preparation of microsphere washing solution: The volume ratio of 0.1 mol/l PBS buffer:purified water=1:9 was used to prepare 500 mL of PBS buffer, pH 7.4. 2.5 g of BSA was added, well mixed, and dissolved, to obtain a microsphere washing solution.

The magnetic microspheres after warm were added into a beaker, then placed on a magnet for precipitation, had the supernatant drained, added with 5× microsphere washing solution for stirring and cleaning, then placed on the magnet until the supernatant became clear, and had the supernatant discarded. The washing step was repeated for four times.

Suspension of magnetic microspheres: After washing, the magnetic microspheres were added into a BSA aqueous solution with a coating volume (5 g/L, containing 1 g/L sodium azide) to obtain a suspension of magnetic microspheres with a suspension concentration of 20 mg/mL, i.e., a suspension of magnetic microspheres coated with streptavidin.

Preparation Example 3: Preparing a Suspension of Magnetic Microspheres Coated with FITC Monoclonal or Polyclonal Antibodies The immunomagnetic microspheres used in this preparative procedure was chosen to be a suspension of nanomagnetic microspheres at a concentration of 100 mg/mL with a hydroxyl group of 95 mg KOH/g, manufactured by Merck.

Preparation of solution A (pH3.6 acetate buffer): 2.55 g of sodium acetate trihydrate was weighed, dissolved in 4500 mL of purified water, combined with 14 mL of acetic acid, mixed well, and added with purified water to a constant volume of 5000 mL (pH 3.6).

The magnetic microspheres were suspended in the above-mentioned pH 3.6 acetate buffer with a volume equivalent to the coating volume so that the concentration of the magnetic microspheres was 20 mg/mL. CMC was added to a concentration of 10 mg/mL. FITC monoclonal or polyclonal antibodies was added to the resulting solution in a weight ratio of 1 mg:12 μg (resulting solution: FITC monoclonal or polyclonal antibodies), and reacted in a constant temperature shock water bath at 37° C. for 24 hours.

Preparation of microsphere washing solution: The volume ratio of 0.1 mol/l PBS buffer:purified water=1:9 was used to prepare 500 mL of PBS buffer, pH 7.4. 2.5 g of BSA was added, well mixed, and dissolved, to obtain a microsphere washing solution.

The magnetic microspheres after warm were added into a beaker, then placed on a magnet for precipitation, had the supernatant drained, added with 5× microsphere washing solution for stirring and cleaning, then placed on the magnet until the supernatant became clear, and had the supernatant discarded. The washing step was repeated for four times.

Suspension of magnetic microspheres: After washing, the magnetic microspheres were added into a BSA aqueous solution with a coating volume (5 g/L, containing 1 g/L sodium azide) to obtain a suspension of magnetic microspheres with a suspension concentration of 20 mg/mL, i.e., a suspension of magnetic microspheres coated with FITC monoclonal or polyclonal antibodies.

Preparation Example 4: Preparation of cTnI Monoclonal or Polyclonal Antibody Solution Labeled with ABEI Preparation of dialysate (solution F): In a 5000 mL beaker, 14.31 g of $Na_2CO_3$ and 26.46 g of $NaHCO_3$ were added and the volume of the solution was adjusted to 4500 mL with water. Prepared solution F was placed in a magnetic stirrer for later use.

A dialysis bag with an interception capacity of 14000 was chosen and a proper size was measured for later use. 1 mg of cTnI monoclonal antibody or polyclonal antibody was adjusted to 1 mL with 0.1 mol/L of carbonate buffer (pH9.5, solution F), placed in the dialysate and dialyzed for 2 hours, while being stirred at 400 rpm. The dialyzed solution was put into a small white bottle (1 mL per flask) and 300 μg of ABEI-hemisuccinamic acid-N-hydroxysuccinimide ester was added and reacted at 37° C. for 2 hours to obtain a solution of cTnI antibody labeled with ABEI.

A G-25 gel column was mounted and eluted with purified water, and the reaction solution was equilibrated with PBS buffer solution of pH 7.4.

Following equilibration of gel column elution, the ABEI-labeled cTnI antibody solution was purified by the column and the peaked solution was collected.

The collected protein solution was added with an equal volume of 0.5 g/mL of BSA protection solution to obtain the cTnI monoclonal or polyclonal antibody solution labeled with ABEI.

Preparation Example 5: Preparation of Biotinylated Solution Labeled with cTnI Monoclonal or Polyclonal Antibody Preparation of dialysate (solution F): In a 5000 mL beaker, 14.31 g of $Na_2CO_3$ and 26.46 g of $NaHCO_3$ were added and the volume of the solution was adjusted to 4500 mL with water. Prepared solution F was placed in a magnetic stirrer for later use.

A dialysis bag with an interception capacity of 14000 was chosen and a proper size was measured for later use. 1 mg of cTnI monoclonal antibody or polyclonal antibody was adjusted to 1 mL with 0.1 mol/L of carbonate buffer (pH9.5, solution F), poured into the dialysis bay with the other end of the bag tied tightly, placed in the dialysate, and dialyzed for 2 hours, while being stirred at 400 rpm.

The activated biotin was dissolved in DMF, and the mixture was allowed to react for 2 h in a molar ratio of 20:1 of biotin to cTnI monoclonal antibody or polyclonal antibody.

The reaction solution was dialyzed using 0.1 mol/L PBS for 24 hours at 4° C. to prepare a biotinylated solution of cTnI monoclonal antibody or polyclonal antibody.

Preparation Example 6: Preparation of FITC Solution Labeled with cTnI Monoclonal or Polyclonal Antibody Preparation of dialysate (solution F): In a 5000 mL beaker, 14.31 g of $Na_2CO_3$ and 26.46 g of $NaHCO_3$ were added and the volume of the solution was adjusted to 4500 mL with water. Prepared solution F was placed in a magnetic stirrer for later use.

A dialysis bag with an interception capacity of 14000 was chosen and a proper size was measured for later use. 1 mg of cTnI monoclonal antibody or polyclonal antibody was adjusted to 1 mL with 0.1 mol/L of carbonate buffer (pH9.5, solution F), poured into the dialysis bay with the other end of the bag tied tightly, placed in the dialysate and dialyzed for 2 hours, while being stirred at 400 rpm.

The dialyzed solution was put into a small white bottle (1 mL per flask) and 100 μg of FITC was added and reacted at RT for 2 hours to obtain a FITC solution labeled with cTnI monoclonal or multiclonal antibodies.

PBS buffer solution (pH 7.4) was prepared as an equilibrium liquid for the chromatography column, which was rinsed with purified water for 24 hours, equilibrated by connecting the equilibrium liquid with the chromatography column for 30 minutes. The fluid of the upper surface was then drained, and the FITC solution labeled with cTnI monoclonal or polyclonal antibody was added. The surface fluid was drained again. An appropriate amount of equilibrium liquid was added, the upper and lower tubings were connected, with the lower end connected to a nucleic acid protein detector (preheated for 2 hours before purification) to adjust the brightness and accuracy. After zeroing, liquid in the time period of the peak was collected, i.e., the FITC solution labeled with cTnI monoclonal or polyclonal antibody.

Preparation Example 7: Preparation of Streptavidin Solution Labeled with cTnI Monoclonal or Polyclonal Antibody Preparation of dialysate (solution F): In a 5000 mL beaker, 14.31 g of $Na_2CO_3$ and 26.46 g of $NaHCO_3$ were added and the volume of the solution was adjusted to 4500 mL with water. Prepared solution F was placed in a magnetic stirrer for later use.

A dialysis bag with an interception capacity of 14000 was chosen and a proper size was measured for later use. 1 mg of cTnI monoclonal antibody or polyclonal antibody was adjusted to 1 mL with 0.1 mol/L of carbonate buffer (pH9.5, solution F), poured into the dialysis bay with the other end of the bag tied tightly, placed in the dialysate and dialyzed for 2 hours, while being stirred at 400 rpm.

The dialyzed solution was put into a small white bottle (1 mL per flask) and 50 μg of streptavidin was added and reacted at 37° C. for 2 hours to obtain a streptavidin solution labeled with cTnI antibody labeled.

A G-25 gel column was mounted and eluted with purified water, and equilibrated with PBS buffer solution of pH 7.4.

Following equilibration of gel column elution, the streptavidin labeled with cTnI antibody solution was purified by the column and the peaked solution was collected.

The collected protein solution was added with an equal volume of 0.5 g/mL of BSA protection solution to obtain the product.

Preparation Example 8: Preparation of FITC Monoclonal or Polyclonal Antibody Solution Labeled with cTnI Monoclonal or Polyclonal Antibody Preparation of dialysate (solution F): In a 5000 mL beaker, 14.31 g of $Na_2CO_3$ and 26.46 g of $NaHCO_3$ were added and the volume of the solution was adjusted to 4500 mL with water. Prepared solution F was placed in a magnetic stirrer for later use.

A dialysis bag with an interception capacity of 14000 was chosen and a proper size was measured for later use. 1 mg of cTnI monoclonal antibody or polyclonal antibody was adjusted to 1 mL with 0.1 mol/L of carbonate buffer (pH9.5, solution F), poured into the dialysis bay with the other end of the bag tied tightly, placed in the dialysate and dialyzed for 2 hours, while being stirred at 400 rpm. The dialyzed solution was put into a small white bottle (1 mL per flask) and 50 μg of FITC monoclonal or polyclonal antibody solution was added and reacted at 37° C. for 2 hours to obtain a FITC monoclonal or polyclonal antibody solution labeled with cTnI antibody.

A G-25 gel column was mounted and eluted with purified water, and equilibrated with PBS buffer solution of pH 7.4.

Following equilibration of gel column elution, the FITC monoclonal or polyclonal antibody solution labeled with cTnI antibody solution was purified by the column and the peaked solution was collected.

The collected protein solution was added with an equal volume of 0.5 g/mL of BSA protection solution to obtain the product.

Preparation Example 9: Preparation of Biotinylated ABEI Solution

Preparation of dialysate (solution F): In a 5000 mL beaker, 14.31 g of $Na_2CO_3$ and 26.46 g of $NaHCO_3$ were added and the volume of the solution was adjusted to 4500 mL with water. Prepared solution F was placed in a magnetic stirrer for later use.

A dialysis bag with an interception capacity of 14000 was chosen and a proper size was measured for later use. 1 mg of biotin was adjusted to 1 mL with 0.1 mol/L of carbonate buffer (pH9.5, solution F), poured into the dialysis bay with the other end of the bag tied tightly, placed in the dialysate and dialyzed for 2 hours, while being stirred at 400 rpm. The dialyzed solution was put into a small white bottle (1 mL per flask) and 300 μg of ABEI-hemisuccinamic acid-N-hydroxysuccinimide ester was added and reacted at 37° C. for 2 hours to obtain a biotinylated ABEI solution.

A G-25 gel column was mounted and eluted with purified water, and equilibrated with PBS buffer solution of pH 7.4.

Following equilibration of gel column elution, the biotinylated ABET solution was purified by the column and the peaked solution was collected.

The collected protein solution was added with an equal volume of 0.5 mg/mL of BSA protection solution to obtain the product.

Preparation Example 10: Preparation of FITC-Labeled ABEI Solution

Preparation of dialysate (solution F): In a 5000 mL beaker, 14.31 g of $Na_2CO_3$ and 26.46 g of $NaHCO_3$ were added and the volume of the solution was adjusted to 4500 mL with water. Prepared solution F was placed in a magnetic stirrer for later use.

A dialysis bag with an interception capacity of 14000 was chosen and a proper size was measured for later use. 1 mg of FITC was adjusted to 1 mL with 0.1 mol/L of carbonate buffer (pH9.5, solution F), had the other end tied tightly, placed in the dialysate and dialyzed for 2 hours, while being stirred at 400 rpm.

The dialyzed solution was put into a small white bottle (1 mL per flask) and 300 μg of ABEI-hemisuccinamic acid-N-hydroxysuccinimide ester was added and reacted at 37° C. for 2 hours.

A G-25 gel column was mounted and eluted with purified water, and equilibrated with PBS buffer solution of pH 7.4.

Following equilibration of gel column elution, the FITC-labeled ABEI was purified by the column and the peaked solution was collected.

The collected protein solution was added with an equal volume of 0.5 g/mL of BSA protection solution to obtain the product.

Preparation Example 11: Preparation of Diluent

In 200 mL of purified water, 5 g of BSA, 300 mL of fresh bovine serum, 50 mL of goat serum, 10 mL of horse serum, 3.08 g of dithiothreitol, 6.05 g of tris (hydroxymethyl) aminomethane, 2.31 g of hydrated 2-morpholinoethanesulfonic acid, 10 mL of ethylene glycol, 50 mL of glycerol, 0.5 mL of Tween-80, 2 g of casein, 1 g of disodium ethylenediaminetetraacetate, and 1 g of sodium azide were added, adjusted with purified water to a total volume of 1000 mL, fully mixed, filtrated with a 0.4 μm filter membrane, and stored for later use. The components could be proportionally increased for different preparation quantity.

Preparation Example 12: Preparation of High and Low Point Calibrator Solutions The cTnI standards were combined with 50% bovine serum product to prepare high and low point calibrator solutions at 17668.000 pg/mL and 34.000 pg/mL, respectively.

In the following examples:

The first anti-cTnI antibody and the second anti-cTnI antibody used below: all manufactured by Hytest.

Goat anti-FITC polyclonal antibody: manufactured by Jackson, US.

ABEI: manufactured by Shenzhen New Industrial Biomedical Co., Ltd.

FITC: manufactured by Sigma, US.

cTnI standards: manufactured by Meridian Life Science, Inc.

The magnetic microspheres were produced by Shenzhen New Industrial Biomedical Engineering Co., Ltd. with an 80% particle size distribution of 1-5 μm, settling time of 10-15 seconds under magnetization intensity of 4000 Gauss, and a protein adsorption concentration of 0.8 mg-1.2 mg under a BSA of 30 mg.

Biotin, streptavidin: manufactured by Biosources, US.

Maglumi 2000 Chemiluminescence Analyzer: manufactured by Shenzhen New Industrial Biomedical Engineering Co., Ltd.

Example 1

Kit 1 was prepared by the following steps:

Two cTnI antibodies capable of respectively binding to the cTnI amino acid segments 18 to 28 and 83 to 93 were used as the first anti-cTnI antibody, and labeled with ABEI according to the procedure of Preparation Example 4 above, to obtain a first anti-cTnI antibody solution labeled with ABEI. The total concentration of the first anti-cTnI antibody was 300 ng/mL and the ABEI concentration was 30 pg/mL.

Two cTnI antibodies capable of respectively binding to the cTnI amino acid segments 41 to 49 and 190 to 196 were used as the second anti-cTnI antibody, and coated on magnetic microspheres according to the procedure of Preparation Example 1 above, to obtain a second anti-cTnI antibody solution coated on magnetic microspheres. The total concentration of the second anti-cTnI antibody was 5 μg/mL and the concentration of the magnetic microspheres was 1 mg/mL.

The diluents were prepared according to Preparation Example 11.

The low and high point calibrator solutions were prepared according to Preparation Example 12, at a concentration of 34.000 pg/mL and 17668.000 pg/mL, respectively.

The above solutions also contained BSA of 1 g/mL and NaN$_3$ of 2 mg/mL.

Example 2

Kit 2 was prepared by the following steps:

Two cTnI antibodies capable of respectively binding to the cTnI amino acid segments 26 to 35 and 83 to 93 were used as the first anti-cTnI antibody, and labeled with ABEI according to the procedure of Preparation Example 4 above, to obtain a first anti-cTnI antibody solution labeled with ABEI. The total concentration of the first anti-cTnI antibody was 300 ng/mL and the ABEI concentration was 30 pg/mL.

Two cTnI antibodies capable of respectively binding to the cTnI amino acid segments 41 to 49 and 169 to 178 were used as the second anti-cTnI antibody, and a solution of the biotinylated second anti-cTnI antibody were prepared according to the procedure of Preparation Example 5 above. The total concentration of the second anti-cTnI antibody was 300 ng/mL and the biotin concentration was 30 pg/mL.

Streptavidin solution coated on magnetic microspheres was prepared as described above in Preparation Example 2. The streptavidin concentration was 10 μg/mL and the concentration of magnetic microspheres was 1 mg/mL.

The diluents were prepared according to Preparation 11.

The low and high point calibrator solutions were prepared according to Preparation Example 12, at a concentration of 34.000 pg/mL and 17668.000 pg/mL, respectively.

The above solutions also contained BSA of 1 g/mL and NaN$_3$ of 2 mg/mL.

Example 3

A suspension of magnetic microspheres coated with goat anti-FITC polyclonal antibody was prepared as in Preparation Example 3 above.

A solution of the first anti-cTnI antibody labeled with ABEI was prepared as described above in Preparation Example 4 using the first anti-cTnI antibody in Example 1.

A second anti-cTnI antibody-labeled FITC solution was prepared as described above in Preparation Example 6 using the second anti-cTnI antibody in Example 1.

A diluent was prepared according to Preparation Example 11 above.

High and low point calibration solutions were prepared according to Preparation Example 12 above.

Each of the solutions prepared as described above constitutes the components of Kit 3 provided in the present example.

Example 4

A suspension of magnetic microspheres coated with the second anti-cTnI antibody was prepared as in Preparation Example 1 above using the second anti-cTnI antibody in Example 1.

A solution of streptavidin labeled with the first anti-cTnI antibody was prepared as described above in Preparation Example 7 using the first anti-cTnI antibody in Example 1.

A biotinylated ABEI solution was prepared as described above in Preparation Example 9.

A diluent was prepared according to Preparation Example 11 above.

High and low point calibration solutions were prepared according to Preparation Example 12 above.

Each of the solutions prepared as described above constitutes the components of Kit 4 provided in the present example.

Example 5

A suspension of magnetic microspheres coated with the second anti-cTnI antibody was prepared as in Preparation Example 1 above using the second anti-cTnI antibody in Example 1.

A solution of goat anti-FITC polyclonal antibody labeled with the first anti-cTnI antibody was prepared as described above in Preparation Example 8 using the first anti-cTnI antibody in Example 1.

A FITC-labeled ABEI solution was prepared as described above in Preparation Example 10.

A diluent was prepared according to Preparation Example 11 above.

High and low point calibration solutions were prepared according to Preparation Example 12 above.

Each of the solutions prepared as described above constitutes the components of Kit 5 provided in the present example.

Example 6

A suspension of magnetic microspheres coated with goat anti-FITC polyclonal antibody was prepared as in Preparation Example 3 above.

A FITC solution labeled with the second anti-cTnI antibody was prepared as in Preparation Example 6 above using the second anti-cTnI antibody in Example 2.

A solution of streptavidin labeled with the first anti-cTnI antibody was prepared as described above in Preparation Example 7 using the first anti-cTnI antibody in Example 2.

A biotinylated ABEI solution was prepared as described above in Preparation Example 9.

A diluent was prepared according to Preparation Example 11 above.

High and low point calibration solutions were prepared according to Preparation Example 12 above.

Each of the solutions prepared as described above constitutes the components of Kit 6 provided in the present example.

Example 7

A solution of magnetic microspheres coated with streptavidin was prepared as in Preparation Example 2 above.

A biotinylated solution labeled with the second anti-cTnI antibody was prepared as in Preparation Example 5 above using the second anti-cTnI antibody in Example 2.

A solution of goat anti-FITC polyclonal antibody labeled with the second anti-cTnI antibody was prepared as described above in Preparation Example 8 using the first anti-cTnI antibody in Example 2.

A FITC-labeled ABEI solution was prepared as described above in Preparation Example 10.

A diluent was prepared according to Preparation Example 11 above.

High and low point calibration solutions were prepared according to Preparation Example 12 above.

Each of the solutions prepared as described above constitutes the components of Kit 6 provided in the present example.

Example 8

The cTnI concentrations in the samples were examined using Kit 1 prepared as described above in Example 1 and a Maglumi 2000 chemiluminescence immunoassay analyzer.

Specifically, the cTnI concentration in a sample is measured according to the following procedure:

A. Add 100 μL of a subject sample, high and low point calibrators to the reaction cups;

B. Add 100 μL of the diluent for reducing non-specific binding;

C. Add 20 μL of cTnI antibody solution coated on magnetic microspheres;

D. Add 100 μL of ABEI-labeled cTnI antibody solution;

E. Keep in a 37° C. temperature bath for 35 min, and 3× wash in magnetic environment;

F. Add 200 μL system washing solution (Shenzhen New Industrial Biomedical Engineering Co., Ltd., Item No. 130299005M);

G. Keep in a 37° C. temperature bath for 35 min, and 3× wash in magnetic environment;

H. Add the chemiluminescent exciters (Shenzhen New Industrial Biomedical Engineering Co., Ltd., Item No. 130299004M) to detect the light signal intensity;

I. Based on the detected light signal intensity, automatically calculate the cTnI concentration of the subject sample based on the 10-point standard curve corrected by the reference standards.

The 10-point standard curve of the kit was prepared by diluting the cTnI standards into the following ten concentrations using the prepared diluent: 0.000 pg/mL, 12.000 pg/mL, 34.000 pg/mL, 97.000 pg/mL, 275.000 Pg/mL, 780.000 pg/mL, 2206.000 pg/mL, 6243.000 pg/mL, 17668.000 pg/mL, 50000.000 pg/mL. And the analyzer was used to determine the light intensities of the standard solutions at the ten concentrations of, with the instrument automatically performing fitting to generate a 10-point standard curve for the kit.

The $9^{th}$ point (17668.000 pg/mL) and the third point (34.000 pg/mL) of the 10-point standard curve were used as the high and low point calibrators of the kit during use. When the kit is used, the instrument will automatically correct the ten point standard curve by calibration with the high point and low point calibrators.

Verification of Analytical Sensitivity:

Determination of the analytical sensitivity follows the "EP17-A2-Guideline for the Evaluation of Detection Capability" issued by American Society for Clinical Laboratory Standards Association (CLSI). The prepared diluent (blank sample) was used as the subject sample, repeated 20 times, and the analytical sensitivity was calculated according to the mean and standard deviation of the measurements (M+2SD). The results are shown in Table 1.

Verification of Functional Sensitivity:

Functional sensitivity was also determined following the "EP17-A2-Guideline for the Evaluation of Detection Capability" issued by the American Society for Clinical Laboratory Standards (CLSI). The cTnI standards were prepared into five low-concentration samples using the diluent as the solvent, which were measured repeated 8 times per day for 5 days. The power function ($CV\% = C_0^{C_1}$) was fitted to the mean and CV % of the measurements of each sample, and the corresponding analyte concentration at CV %=20% was obtained by the power function curve as the functional sensitivity (FS). The results are shown in Table 2.

Verification of Linear Range:

The linear range of was determined following the "EP6-A: linear quantitative measurement methods: a statistical method, approved guidelines" issued by the American Society for Clinical Laboratory Standards (CLSI). The cTnI standards were dissolved with diluent and prepared into a high concentration solution sample (H). A series of linear solutions was prepared using the diluent (i.e., blank sample, L) and the high concentration solution sample (H) in different volume ratios. The prepared series of cTnI linear solutions were tested with the kit of Example 1. The results of the test data are shown in Table 7. The linear data is plotted in a fitting curve with the linear data of Example 9 below, and the results are shown in FIG. 2.

Example 9

The assay method was substantially the same as that of Example 8, except that step B in Example 8 was omitted.

The results of analytical sensitivity, functional sensitivity, and linearity range are shown in Tables 1, 3 and 6, respectively. The fitting curve of the linear data with the linear data of Example 8 is shown in FIG. 2.

Example 10

The cTnI concentrations in the samples were examined using Kit 2 prepared as described above in Example 2 and a Maglumi 2000 chemiluminescence immunoassay analyzer.

Specifically, the cTnI concentration in a sample is measured according to the following procedure:

A. Add 100 μL of a subject sample, high and low point calibrators to the reaction cups;

B. Add 100 μL of the diluent for reducing non-specific binding;

C. Add 20 μL of streptavidin solution coated on magnetic microspheres;

D. Add 100 μL of biotinlyated cTnI antibody solution;

E. Add 100 μL of ABEI labeled with cTnI monoclonal or polyclonal antibody;

F. Keep in a 37° C. temperature bath for 35 min, and wash in magnetic environment for 3 times;

G. Add 200 μL system washing solution;

H. Keep in a 37° C. temperature bath for 35 min, and wash in magnetic environment for 3 times;

I. Add luminescent substrate to detect the light signal intensity;

J. Based on the detected light signal intensity, automatically calculate the cTnI concentration of the subject sample based on the 10-point standard curve corrected by the reference standards.

The analytical sensitivity, the functional sensitivity and the linearity range were determined according to the above procedure, the subject samples were the same as in Example 8, and the results are shown in Tables 1, 4 and 7, respectively. The fitting curve of the linear data with the linear data of Example 11 is shown in FIG. 3.

Example 11

The assay method was substantially the same as in Example 10, except that step b in Example 10 was omitted.

The results of analytical sensitivity, functional sensitivity and linearity range are shown in Tables 1, 5 and 7, respectively. The fitting curve of the linear data with the linear data of Example 10 is shown in FIG. 3.

Comparative Example 1

The assay samples for the analytical sensitivity, functional sensitivity and linearity range as prepared in Example 8 were measured using the enzyme-free kit manufactured by Nanjing Getein Biotechnology Co., Ltd., and the results are shown in Tables 1, 6 and 9.

TABLE 1

Analytical Sensitivity Results

| Number of Test | Example 8 (pg/mL) | Example 9 (pg/mL) | Example 10 (pg/mL) | Example 11 (pg/mL) | Comparative Example 1 (pg/mL) |
|---|---|---|---|---|---|
| 1 | 0.381 | 18.36 | 0.555 | 21.529 | 22.78 |
| 2 | 0.378 | 21.88 | 0.571 | 26.380 | 21.57 |
| 3 | 0.454 | 18.13 | 0.531 | 22.262 | 23.56 |
| 4 | 0.758 | 20.15 | 0.879 | 20.651 | 24.32 |
| 5 | 0.577 | 21.54 | 0.770 | 17.577 | 23.90 |
| 6 | 0.549 | 19.95 | 0.245 | 24.580 | 25.29 |
| 7 | 0.414 | 21.51 | 0.486 | 22.576 | 24.19 |
| 8 | 0.528 | 20.73 | 0.378 | 25.053 | 23.65 |
| 9 | 0.532 | 19.32 | 0.919 | 20.012 | 22.06 |
| 10 | 0.348 | 23.66 | 0.271 | 19.434 | 21.26 |
| 11 | 0.877 | 19.70 | 0.494 | 21.707 | 21.76 |
| 12 | 0.545 | 23.36 | 0.503 | 20.916 | 23.49 |
| 13 | 0.567 | 18.01 | 0.981 | 23.602 | 23.99 |
| 14 | 0.610 | 19.93 | 0.469 | 26.033 | 24.53 |
| 15 | 0.628 | 22.54 | 0.846 | 20.048 | 22.64 |
| 16 | 0.616 | 20.90 | 0.691 | 23.607 | 21.13 |
| 17 | 0.191 | 20.80 | 0.207 | 26.831 | 23.83 |
| 18 | 0.950 | 21.63 | 0.621 | 18.223 | 23.43 |
| 19 | 0.429 | 20.81 | 0.530 | 21.759 | 25.23 |
| 20 | 0.719 | 22.67 | 0.831 | 21.457 | 24.43 |
| Mean (M) | 0.55 | 20.78 | 0.59 | 22.21 | 23.35 |
| SD | 0.18 | 1.63 | 0.23 | 2.63 | 1.26 |
| M + 2SD | 0.92 | 24.03 | 1.04 | 27.47 | 25.87 |

The analytical sensitivity is the mean of the test results plus twice the standard deviation, which is M+2SD.

As can be seen from the test results, due to the addition of a diluent reducing the specific binding of the reaction, the analytical sensitivity of Examples 8 and 10 was significantly higher than that of Example 9, Example 11, and Comparative Example 1 with no diluent added. At the same time, the analytical sensitivity of Example 8 reached 0.92 pg/mL, which could be of great help to the clinical application of AMI.

TABLE 2

Functional Sensitivity Results of Example 8

| Number of Test | Sample 1 1 pg/mL | Sample 2 2 pg/mL | Sample 3 3 pg/mL | Sample 4 4 pg/mL | Sample 5 5 pg/mL |
|---|---|---|---|---|---|
| 1 | 1.514 | 2.186 | 2.991 | 4.040 | 5.104 |
| 2 | 1.205 | 2.577 | 2.737 | 3.746 | 5.065 |
| 3 | 0.585 | 1.610 | 3.289 | 3.498 | 5.216 |
| 4 | 1.201 | 1.661 | 3.239 | 4.005 | 4.864 |
| 5 | 0.781 | 1.978 | 2.795 | 3.479 | 5.235 |
| 6 | 2.329 | 2.762 | 3.408 | 3.312 | 4.818 |
| 7 | 0.201 | 1.062 | 2.832 | 3.854 | 4.961 |
| 8 | 1.317 | 1.981 | 3.846 | 4.242 | 4.748 |
| 9 | 0.978 | 1.565 | 3.323 | 4.372 | 4.968 |
| 10 | 1.768 | 1.995 | 3.241 | 4.033 | 5.672 |
| 11 | 0.608 | 1.577 | 3.342 | 4.314 | 4.667 |
| 12 | 1.486 | 1.856 | 3.262 | 3.933 | 5.960 |
| 13 | 0.910 | 1.784 | 3.612 | 4.564 | 4.833 |
| 14 | 0.120 | 1.778 | 3.176 | 3.926 | 5.354 |
| 15 | 1.053 | 2.590 | 2.722 | 4.546 | 4.682 |
| 16 | 1.776 | 2.027 | 2.453 | 3.598 | 5.161 |
| 17 | 0.068 | 1.300 | 2.833 | 3.352 | 4.870 |
| 18 | 1.230 | 2.009 | 2.606 | 3.786 | 4.610 |
| 19 | 0.982 | 1.711 | 2.811 | 4.498 | 4.249 |
| 20 | 0.747 | 1.048 | 3.457 | 3.315 | 5.357 |
| 21 | 0.805 | 2.634 | 3.491 | 3.994 | 4.842 |
| 22 | 1.903 | 2.125 | 3.026 | 3.668 | 4.313 |
| 23 | 0.878 | 2.177 | 2.808 | 2.915 | 5.370 |
| 24 | 0.817 | 2.283 | 3.396 | 4.478 | 5.215 |
| 25 | 1.529 | 2.423 | 3.867 | 3.899 | 4.173 |
| 26 | 1.273 | 1.968 | 3.203 | 3.766 | 5.010 |
| 27 | 0.023 | 2.606 | 3.209 | 4.390 | 4.984 |
| 28 | 0.747 | 2.026 | 3.021 | 3.808 | 5.019 |
| 29 | 0.422 | 1.344 | 2.898 | 4.784 | 5.786 |
| 30 | 0.977 | 2.046 | 3.185 | 4.368 | 4.797 |
| 31 | 0.932 | 2.794 | 2.287 | 4.761 | 4.804 |
| 32 | 1.795 | 1.836 | 3.575 | 3.302 | 5.047 |
| 33 | 1.014 | 2.191 | 2.701 | 3.869 | 4.703 |
| 34 | 1.680 | 1.609 | 3.249 | 4.142 | 4.538 |
| 35 | 0.954 | 2.028 | 2.400 | 5.038 | 5.434 |
| 36 | 0.649 | 1.902 | 2.973 | 3.850 | 5.918 |
| 37 | 0.868 | 2.019 | 3.121 | 3.703 | 5.313 |

TABLE 2-continued

Functional Sensitivity Results of Example 8

| Number of Test | Sample 1 1 pg/mL | Sample 2 2 pg/mL | Sample 3 3 pg/mL | Sample 4 4 pg/mL | Sample 5 5 pg/mL |
|---|---|---|---|---|---|
| 38 | 0.099 | 2.580 | 3.958 | 3.699 | 5.115 |
| 39 | 0.938 | 2.383 | 3.325 | 4.046 | 5.051 |
| 40 | 1.019 | 1.926 | 3.481 | 3.568 | 4.562 |
| Mean (M, pg/mL) | 1.000 | 1.999 | 3.129 | 3.962 | 5.010 |
| SD | 0.5419 | 0.4316 | 0.3921 | 0.4636 | 0.4101 |
| CV % | 54.20% | 21.59% | 12.53% | 11.70% | 8.19% |
| F.S (CV = 20%) | | | 2.28 pg/mL | | |

TABLE 3

Functional Sensitivity Results of Example 9

| Number of Test | Sample 1 20 pg/mL | Sample 2 50 pg/mL | Sample 3 80 pg/mL | Sample 4 100 pg/mL | Sample 5 120 pg/mL |
|---|---|---|---|---|---|
| 1 | 2.436 | 25.122 | 78.342 | 96.316 | 113.932 |
| 2 | 14.250 | 31.994 | 67.534 | 109.263 | 105.940 |
| 3 | 33.812 | 60.446 | 67.445 | 123.420 | 121.490 |
| 4 | 16.583 | 54.070 | 67.220 | 85.807 | 125.276 |
| 5 | 18.534 | 33.997 | 108.346 | 113.375 | 121.567 |
| 6 | 46.193 | 50.543 | 71.998 | 87.842 | 130.214 |
| 7 | 16.389 | 38.905 | 76.207 | 124.688 | 129.959 |
| 8 | 22.073 | 76.085 | 76.206 | 97.526 | 103.221 |
| 9 | 30.290 | 44.645 | 74.725 | 113.406 | 116.639 |
| 10 | 33.579 | 71.182 | 91.679 | 89.354 | 116.033 |
| 11 | 35.247 | 62.914 | 81.911 | 113.873 | 128.601 |
| 12 | 33.658 | 44.344 | 79.019 | 81.563 | 126.471 |
| 13 | 24.779 | 46.627 | 100.564 | 86.418 | 125.160 |
| 14 | 27.394 | 46.137 | 58.743 | 98.967 | 125.255 |
| 15 | 25.029 | 78.863 | 102.440 | 113.446 | 107.070 |
| 16 | 36.185 | 51.470 | 75.896 | 112.013 | 128.566 |
| 17 | 10.100 | 28.796 | 93.664 | 104.918 | 127.714 |
| 18 | 17.035 | 70.944 | 64.036 | 82.793 | 114.881 |
| 19 | 4.547 | 48.525 | 91.796 | 109.014 | 114.311 |
| 20 | 20.181 | 48.830 | 65.257 | 123.561 | 120.541 |
| 21 | 18.534 | 64.066 | 71.188 | 78.663 | 110.548 |
| 22 | 2.941 | 43.864 | 85.066 | 105.266 | 111.492 |
| 23 | 49.612 | 43.719 | 85.725 | 102.602 | 107.186 |
| 24 | 28.189 | 50.548 | 82.989 | 117.261 | 118.150 |
| 25 | 27.879 | 57.085 | 92.802 | 88.969 | 119.647 |
| 26 | 19.331 | 63.056 | 64.554 | 85.254 | 105.161 |
| 27 | 30.899 | 28.558 | 62.680 | 88.817 | 112.749 |
| 28 | 23.551 | 56.909 | 82.726 | 117.738 | 125.349 |
| 29 | 17.604 | 49.464 | 74.662 | 77.774 | 106.769 |
| 30 | 33.742 | 53.263 | 51.987 | 85.614 | 122.249 |
| 31 | 0.912 | 46.007 | 76.914 | 96.054 | 123.160 |
| 32 | 5.201 | 71.316 | 81.335 | 110.182 | 125.735 |
| 33 | 3.870 | 37.134 | 67.382 | 122.178 | 133.210 |
| 34 | 16.514 | 34.627 | 99.048 | 79.825 | 131.143 |
| 35 | 42.633 | 54.916 | 72.232 | 101.029 | 127.057 |
| 36 | 2.626 | 62.521 | 86.289 | 105.885 | 104.977 |
| 37 | 17.268 | 42.190 | 93.024 | 110.887 | 114.131 |
| 38 | 3.097 | 49.330 | 65.602 | 119.826 | 127.286 |
| 39 | 2.418 | 52.149 | 58.656 | 89.504 | 105.073 |
| 40 | 19.443 | 52.502 | 79.012 | 79.970 | 105.151 |
| Mean (M, pg/mL) | 20.542 | 50.692 | 78.173 | 100.772 | 118.477 |
| SD | 13.4651 | 13.0863 | 13.1449 | 14.6801 | 9.0215 |
| CV % | 65.55% | 25.82% | 16.82% | 14.57% | 7.61% |
| F.S (CV = 20%) | | | 64.54 pg/mL | | |

TABLE 4

Functional Sensitivity Results of Example 10

| Number of Test | Sample 1 1 pg/mL | Sample 2 2 pg/mL | Sample 3 3 pg/mL | Sample 4 4 pg/mL | Sample 5 5 pg/mL |
|---|---|---|---|---|---|
| 1 | 0.695 | 2.628 | 2.600 | 3.426 | 5.313 |
| 2 | 1.443 | 2.700 | 2.768 | 4.069 | 4.452 |
| 3 | 1.334 | 2.420 | 3.137 | 4.217 | 4.463 |
| 4 | 1.063 | 1.412 | 2.532 | 4.643 | 5.402 |
| 5 | 1.596 | 1.104 | 2.198 | 3.951 | 5.508 |
| 6 | 0.959 | 2.282 | 2.507 | 3.730 | 4.668 |
| 7 | 0.735 | 1.774 | 3.068 | 4.593 | 5.507 |
| 8 | 0.359 | 2.698 | 2.136 | 3.560 | 5.154 |
| 9 | 0.422 | 1.832 | 2.730 | 3.746 | 4.719 |
| 10 | 0.222 | 2.406 | 3.259 | 2.918 | 4.955 |
| 11 | 1.486 | 1.940 | 2.720 | 3.656 | 4.989 |
| 12 | 1.417 | 2.438 | 3.420 | 4.433 | 4.566 |
| 13 | 1.521 | 1.930 | 3.750 | 3.221 | 5.239 |
| 14 | 0.596 | 2.108 | 3.783 | 3.181 | 4.711 |
| 15 | 1.725 | 2.216 | 2.572 | 3.812 | 4.927 |
| 16 | 0.806 | 1.572 | 3.007 | 3.695 | 5.377 |
| 17 | 0.095 | 2.372 | 2.032 | 3.611 | 5.180 |
| 18 | 0.018 | 1.710 | 3.093 | 3.585 | 5.380 |
| 19 | 2.127 | 1.519 | 3.012 | 3.671 | 4.658 |
| 20 | 2.265 | 1.997 | 2.600 | 3.454 | 5.373 |
| 21 | 0.236 | 1.835 | 3.595 | 4.060 | 5.119 |
| 22 | 1.259 | 1.680 | 3.725 | 4.512 | 4.783 |
| 23 | 0.233 | 1.918 | 2.887 | 3.887 | 5.368 |
| 24 | 1.446 | 2.535 | 2.840 | 3.855 | 4.585 |
| 25 | 0.807 | 2.035 | 2.968 | 4.015 | 4.992 |
| 26 | 0.809 | 1.741 | 2.875 | 3.920 | 4.906 |
| 27 | 1.015 | 1.347 | 2.449 | 3.717 | 5.796 |
| 28 | 1.180 | 1.644 | 2.724 | 4.055 | 5.395 |
| 29 | 0.348 | 2.324 | 2.088 | 4.089 | 4.831 |
| 30 | 1.138 | 1.756 | 3.470 | 3.478 | 5.477 |
| 31 | 0.921 | 2.826 | 2.688 | 3.974 | 5.635 |
| 32 | 1.504 | 2.420 | 3.124 | 3.164 | 5.081 |
| 33 | 0.448 | 1.993 | 2.896 | 3.693 | 4.684 |
| 34 | 1.452 | 2.251 | 2.318 | 4.338 | 5.849 |
| 35 | 0.355 | 3.155 | 3.525 | 3.721 | 4.480 |
| 36 | 0.980 | 2.328 | 2.960 | 3.967 | 4.335 |
| 37 | 1.702 | 2.538 | 3.333 | 4.132 | 5.188 |
| 38 | 1.577 | 1.669 | 2.531 | 4.799 | 5.582 |
| 39 | 0.848 | 1.634 | 2.477 | 3.670 | 4.502 |
| 40 | 1.377 | 2.931 | 3.299 | 3.597 | 4.543 |
| Mean (M, pg/mL) | 1.012 | 2.090 | 2.892 | 3.845 | 5.042 |
| SD | 0.5656 | 0.4685 | 0.4644 | 0.4151 | 0.4118 |
| CV % | 55.89% | 22.41% | 16.06% | 10.79% | 8.17% |
| F.S (CV = 20%) | | | 2.36 pg/mL | | |

TABLE 5

Functional Sensitivity Results of Example 11

| Number of Test | Sample 1 20 pg/mL | Sample 2 50 pg/mL | Sample 3 80 pg/mL | Sample 4 100 pg/mL | Sample 5 120 pg/mL |
|---|---|---|---|---|---|
| 1 | 25.576 | 40.677 | 59.007 | 98.161 | 109.217 |
| 2 | 20.922 | 57.127 | 81.647 | 110.559 | 141.708 |
| 3 | 23.234 | 66.827 | 76.806 | 104.441 | 133.664 |
| 4 | 4.293 | 37.904 | 72.523 | 126.219 | 129.504 |
| 5 | 18.870 | 26.280 | 82.887 | 105.819 | 126.942 |
| 6 | 18.978 | 64.076 | 96.198 | 87.506 | 121.640 |
| 7 | 26.452 | 32.063 | 61.067 | 99.968 | 104.086 |
| 8 | 18.976 | 44.144 | 87.332 | 85.016 | 118.400 |
| 9 | 33.226 | 38.921 | 73.358 | 105.256 | 122.456 |
| 10 | 23.520 | 51.343 | 62.498 | 102.354 | 127.493 |
| 11 | 14.248 | 45.013 | 77.991 | 107.052 | 108.693 |
| 12 | 19.553 | 37.842 | 75.095 | 106.057 | 128.986 |
| 13 | 9.340 | 54.674 | 91.729 | 121.582 | 121.428 |
| 14 | 1.695 | 61.857 | 80.690 | 91.111 | 123.744 |
| 15 | 34.804 | 64.112 | 105.262 | 115.202 | 114.493 |
| 16 | 14.884 | 33.919 | 80.261 | 78.471 | 102.566 |
| 17 | 17.470 | 76.758 | 58.998 | 118.867 | 121.168 |

TABLE 5-continued

Functional Sensitivity Results of Example 11

| Number of Test | Sample 1 20 pg/mL | Sample 2 50 pg/mL | Sample 3 80 pg/mL | Sample 4 100 pg/mL | Sample 5 120 pg/mL |
|---|---|---|---|---|---|
| 18 | 8.968 | 56.621 | 77.033 | 127.616 | 127.029 |
| 19 | 41.658 | 27.734 | 75.339 | 105.493 | 134.804 |
| 20 | 3.764 | 34.718 | 62.304 | 118.923 | 116.524 |
| 21 | 44.461 | 52.642 | 66.098 | 128.902 | 130.971 |
| 22 | 12.701 | 29.316 | 75.603 | 92.398 | 128.154 |
| 23 | 15.098 | 32.881 | 75.070 | 97.745 | 123.744 |
| 24 | 8.233 | 57.805 | 59.208 | 111.344 | 135.271 |
| 25 | 11.872 | 55.831 | 85.265 | 92.396 | 141.157 |
| 26 | 14.281 | 58.959 | 64.798 | 79.753 | 106.971 |
| 27 | 14.471 | 59.405 | 65.011 | 99.080 | 104.861 |
| 28 | 24.975 | 55.655 | 91.215 | 115.676 | 109.060 |
| 29 | 30.716 | 53.966 | 87.967 | 90.112 | 108.873 |
| 30 | 24.021 | 25.581 | 106.529 | 90.093 | 118.165 |
| 31 | 16.988 | 59.762 | 57.457 | 108.888 | 124.619 |
| 32 | 32.515 | 52.939 | 105.254 | 100.902 | 100.553 |
| 33 | 15.296 | 33.884 | 88.063 | 101.556 | 119.268 |
| 34 | 13.051 | 43.337 | 62.675 | 126.224 | 118.724 |
| 35 | 1.219 | 47.987 | 55.867 | 76.931 | 135.946 |
| 36 | 40.094 | 60.048 | 54.895 | 95.974 | 113.412 |
| 37 | 44.484 | 50.404 | 86.347 | 108.802 | 129.505 |
| 38 | 21.769 | 44.343 | 71.136 | 102.062 | 114.030 |
| 39 | 35.107 | 24.786 | 82.917 | 81.126 | 107.109 |
| 40 | 28.235 | 34.485 | 81.040 | 88.531 | 127.855 |
| Mean (M, pg/mL) | 20.348 | 47.166 | 76.511 | 102.604 | 120.820 |
| SD | 12.1315 | 13.2301 | 13.9072 | 14.0110 | 10.8937 |
| CV % | 59.62% | 28.05% | 18.18% | 13.66% | 9.02% |
| F.S (CV = 20%) | | | 65.75 pg/mL | | |

TABLE 6

Functional sensitivity results of Comparative Example 1

| Number of Test | Sample 1 20 pg/mL | Sample 2 50 pg/mL | Sample 3 80 pg/mL | Sample 4 100 pg/mL | Sample 5 120 pg/mL |
|---|---|---|---|---|---|
| 1 | 9.390 | 52.207 | 91.448 | 93.973 | 120.142 |
| 2 | 17.464 | 39.358 | 99.591 | 104.467 | 118.439 |
| 3 | 17.538 | 62.684 | 68.185 | 103.145 | 110.792 |
| 4 | 15.526 | 49.421 | 75.319 | 103.640 | 116.036 |
| 5 | 12.044 | 58.666 | 76.983 | 105.301 | 116.833 |
| 6 | 7.831 | 34.643 | 77.458 | 96.513 | 122.786 |
| 7 | 27.120 | 55.631 | 107.996 | 108.213 | 126.706 |
| 8 | 27.475 | 53.311 | 69.185 | 98.110 | 108.975 |
| 9 | 6.258 | 71.708 | 92.726 | 100.820 | 123.374 |
| 10 | 15.117 | 60.892 | 57.663 | 92.023 | 122.090 |
| 11 | 22.512 | 44.962 | 84.053 | 102.198 | 114.414 |
| 12 | 11.697 | 34.592 | 60.631 | 100.069 | 126.545 |
| 13 | 20.907 | 42.223 | 94.022 | 95.469 | 117.558 |
| 14 | 9.854 | 49.985 | 66.134 | 92.547 | 122.157 |
| 15 | 11.047 | 55.176 | 84.322 | 102.221 | 109.614 |
| 16 | 19.908 | 30.918 | 82.462 | 94.744 | 122.622 |
| 17 | 6.586 | 39.331 | 66.732 | 101.964 | 113.298 |
| 18 | 34.976 | 45.664 | 82.490 | 96.953 | 116.728 |
| 19 | 18.421 | 51.356 | 58.912 | 105.050 | 117.075 |
| 20 | 16.573 | 52.635 | 76.130 | 103.143 | 123.013 |
| 21 | 12.558 | 51.476 | 86.774 | 98.358 | 119.371 |
| 22 | 17.591 | 45.273 | 87.355 | 92.576 | 126.675 |
| 23 | 32.728 | 50.406 | 87.230 | 106.714 | 124.895 |
| 24 | 19.830 | 54.240 | 95.854 | 106.935 | 119.431 |
| 25 | 26.649 | 37.038 | 71.897 | 95.732 | 124.222 |
| 26 | 31.771 | 45.750 | 84.185 | 102.194 | 118.847 |
| 27 | 33.589 | 48.064 | 76.540 | 101.082 | 123.688 |
| 28 | 35.409 | 47.207 | 77.841 | 106.970 | 119.486 |
| 29 | 16.103 | 36.838 | 98.376 | 94.636 | 112.681 |
| 30 | 14.226 | 37.255 | 75.812 | 98.588 | 113.634 |
| 31 | 15.496 | 31.338 | 77.221 | 101.618 | 120.774 |
| 32 | 15.909 | 29.642 | 102.206 | 102.017 | 126.545 |
| 33 | 7.444 | 40.230 | 92.693 | 93.447 | 113.825 |
| 34 | 9.320 | 40.827 | 59.308 | 99.849 | 121.870 |
| 35 | 35.430 | 28.980 | 88.193 | 99.385 | 115.189 |
| 36 | 11.911 | 28.364 | 71.660 | 107.633 | 119.866 |
| 37 | 9.328 | 53.017 | 102.735 | 94.183 | 119.635 |
| 38 | 24.170 | 55.008 | 64.461 | 102.890 | 122.522 |
| 39 | 13.730 | 55.189 | 74.498 | 97.642 | 119.645 |
| 40 | 24.528 | 47.613 | 111.267 | 99.769 | 122.894 |
| Mean (M, pg/mL) | 18.399 | 46.228 | 81.464 | 100.070 | 119.372 |
| SD | 8.6688 | 10.1328 | 13.8365 | 4.6062 | 4.7488 |
| CV % | 47.12% | 21.92% | 16.98% | 4.60% | 3.98% |
| F.S (CV = 20%) | | | 42.81 pg/mL | | |

The functional sensitivity is the concentration of the corresponding subject sample with a daily repeat CV of 20%.

As can be seen from the test results, due to the addition of a diluent reducing the specific binding of the reaction, the functional sensitivity of Examples 8 and 10 was significantly higher than that of Example 9, Example 11, and Comparative Example 1 with no diluent added. At the same time, the functional sensitivity of the preferable Example 8 reached 2.28 pg/mL, which could be of great help to the clinical diagnosis of AMI.

TABLE 7

Linear range measurement results of Example 8 and Example 9

| Sample Number | Example 8 (pg/mL) | | | Example 9 (pg/mL) | | | Target Value (pg/mL) |
|---|---|---|---|---|---|---|---|
| | Test 1 | Test 2 | Mean | Test 1 | Test 2 | Mean | |
| 1 | 1.03 | 1.11 | 1.07 | 21.68 | 24.12 | 22.9 | 0 |
| 2 | 5061.74 | 5045.58 | 5053.66 | 4958.47 | 4932.91 | 4945.69 | 5000 |
| 3 | 9947.46 | 10089.06 | 10018.26 | 9919.74 | 10237.52 | 10078.63 | 10000 |
| 4 | 14682.70 | 15390.09 | 15036.40 | 14784.55 | 15346.66 | 15065.60 | 15000 |
| 5 | 19772.27 | 20432.15 | 20102.21 | 20420.75 | 19833.60 | 20127.18 | 20000 |
| 6 | 25182.02 | 25079.14 | 25130.58 | 25164.03 | 25395.64 | 25279.83 | 25000 |
| 7 | 30372.10 | 30295.89 | 30334.00 | 29678.80 | 30990.24 | 30334.52 | 30000 |
| 8 | 35238.40 | 35012.64 | 35125.52 | 35078.58 | 35056.68 | 35067.63 | 35000 |
| 9 | 40056.33 | 40402.65 | 40229.49 | 40489.34 | 38772.51 | 39630.92 | 40000 |
| 10 | 45514.87 | 44969.55 | 45242.21 | 44659.29 | 46267.12 | 45463.21 | 45000 |
| 11 | 49508.79 | 50997.35 | 50253.07 | 51643.85 | 49959.06 | 50801.46 | 50000 |

TABLE 8

Linear measurement results of Example 10 and Example 11

| Sample Number | Example 10(pg/mL) | | | Example 11(pg/mL) | | | Target Value (pg/mL) |
|---|---|---|---|---|---|---|---|
| | Test 1 | Test 2 | Mean | Test 1 | Test 2 | Mean | |
| 1 | 1.13 | 0.97 | 1.05 | 22.51 | 23.82 | 23.17 | 0 |
| 2 | 5066.76 | 4962.05 | 5014.40 | 5119.28 | 4906.89 | 5013.09 | 5000 |
| 3 | 9822.31 | 10008.33 | 9915.32 | 9889.99 | 10215.61 | 10052.80 | 10000 |
| 4 | 14713.43 | 15491.40 | 15102.42 | 15523.42 | 14915.52 | 15219.47 | 15000 |
| 5 | 20001.37 | 19944.80 | 19973.08 | 20548.07 | 20008.40 | 20278.23 | 20000 |
| 6 | 25433.67 | 24818.28 | 25125.97 | 25243.80 | 24401.82 | 24822.81 | 25000 |
| 7 | 29367.80 | 30468.66 | 29918.23 | 30326.69 | 29914.32 | 30120.50 | 30000 |
| 8 | 33847.61 | 36516.14 | 35181.88 | 35017.49 | 35233.82 | 35125.66 | 35000 |
| 9 | 40841.55 | 39594.17 | 40217.86 | 40480.71 | 40638.46 | 40559.58 | 40000 |
| 10 | 44993.40 | 45967.35 | 45480.37 | 45325.66 | 44630.03 | 44977.85 | 45000 |
| 11 | 50834.04 | 50989.20 | 50911.62 | 50710.30 | 50399.36 | 50554.83 | 50000 |

TABLE 9

Linear measurement results of Comparative Example 1

| Sample Number | Comparative Example 1 (pg/mL) | | | Target Value (pg/mL) |
|---|---|---|---|---|
| | Test 1 | Test 2 | Mean | |
| 1 | 24.207 | 16.983 | 20.595 | 0 |
| 2 | 4869.31 | 4942.03 | 4905.67 | 5000 |
| 3 | 11414.32 | 10100.69 | 10757.50 | 10000 |
| 4 | 15614.65 | 14798.98 | 15206.82 | 15000 |
| 5 | 21141.23 | 19725.66 | 20433.45 | 20000 |
| 6 | 25634.14 | 24518.38 | 25076.26 | 25000 |
| 7 | 30613.77 | 30470.55 | 30542.16 | 30000 |
| 8 | 33659.92 | 35548.21 | 34604.07 | 35000 |
| 9 | 40333.75 | 39200.82 | 39767.29 | 40000 |
| 10 | 46143.61 | 45674.58 | 45909.09 | 45000 |
| 11 | 53297.58 | 48899.28 | 51098.43 | 50000 |

From the results of Tables 7-9 and FIGS. 2 and 3, it can be seen that the kit provided by the present disclosure has a good linear relationship between the detection value and the theoretical value of the cTnI sample in the concentration range of 0-50000 pg/mL. The addition of diluent had no significant effect on the detection linearity. However, it can be seen from the sensitivity test results above that the addition of diluent can maintain a good linear relationship while improving the detection sensitivity.

In conclusion, the cTnI chemiluminescence immunoassay kit prepared according to the present disclosure can measure linear samples with equivalent to or better measurement results than the existing commercially available ELISA kits used. But according to preferred embodiments of the present disclosure (such as Examples 8 and 10), using the cTnI assay kit prepared in accordance with the present disclosure to measure samples can provide analytical sensitivity and functional sensitivity significantly superior to those of the commercially available enzyme-linked immunosorbant assay kits. Thus, in diagnosis of AMI patients, the cTnI assay kit provided by the present disclosure can provide more accurate and more effective information for diagnosis.

Although the present disclosure has been described in detail, modifications within the spirit and scope of the disclosure will be apparent to those skilled in the art. In addition, it is to be understood that the various aspects, various portions of different embodiments, and various features recited in the present specification may be combined in whole or in part. In the various embodiments described above, those embodiments with reference to another embodiment may be suitably combined with other embodiments, as will be understood by those skilled in the art. Furthermore, it will be understood by those skilled in the art that the foregoing description is by way of example only and is not intended to limit the disclosure.

The invention claimed is:

1. A cardiac troponin I ultrasensitive assay kit, comprising at least one first anti-cardiac troponin I antibody labeled with a trace marker and at least one second anti-cardiac troponin I antibody coated on magnetic microspheres, wherein the at least one first anti-cardiac troponin I antibody and the at least one second anti-cardiac troponin I antibody bind to different binding sites of cardiac troponin I;
   wherein the kit further comprises a diluent comprising the following components: bovine serum albumin, neonatal bovine serum, goat serum, horse serum, dithiothreitol, tris (hydroxymethyl) aminomethane, hydrated 2-morpholinoethanesulfonic acid, ethylene glycol, glycerol, polysorbate 80, casein, and disodium ethylene diaminetetraacetate.

2. The kit according to claim 1, wherein the trace marker is at least one selected from the group consisting of adamantane, luminol, isoluminol and its derivatives, acridinium esters, alkaline phosphatase, and horseradish peroxidase.

3. The kit according to claim 2, wherein the trace marker is N-(4-aminobutyl)-N-ethylisoluminol.

4. The kit according to claim 1, wherein the magnetic microspheres are a complex of Fe2O3 or Fe3O4 magnetic nanoparticles with an organic polymeric material, the magnetic microspheres having a particle diameter of 0.1 to 5 μm; and wherein the magnetic microspheres are optionally modified by surface modification to carry one or more active functional groups.

5. The kit according to claim 1, wherein
   the trace marker directly or indirectly labels the at least one first anti-cardiac troponin I antibody, and the indirect labeling comprises indirect labeling either by a system of fluorescein isothiocyanate and anti-isothiocyanate fluorescein antibody or by a system of streptavidin and biotin;
   the at least one second anti-cardiac troponin I antibody directly or indirectly coats the magnetic microspheres, and the indirect coating of the magnetic microspheres comprises indirect coating either by a system of fluorescein isothiocyanate and anti-isothiocyanate fluorescein antibody or by a system of streptavidin and biotin.

6. The kit according to claim 5, wherein the kit comprises any one selected from the group consisting of A1 to A3 and any one selected from the group consisting of B1-B2, wherein
A1 is a solution of the at least one first anti-cardiac troponin I antibody labeled with a trace marker;
A2 is a streptavidin solution labeled with a trace marker and a solution of the at least one first anti-cardiac troponin I antibody that is biotinylated; and
A3 is a solution of the anti-isothiocyanate fluorescein antibody labeled with a trace marker and a solution of the at least one first anti-cardiac troponin I antibody labeled with fluorescein isothiocyanate; and
B1 is the at least one second anti-cardiac troponin I antibody in solution coated on the magnetic microsphere;
B2 is a streptavidin solution coated on the magnetic microsphere and a solution of the biotinylated at least one second anti-cardiac troponin I antibody; and
B3 is a solution of the anti-isothiocyanate fluorescein antibody coated on the magnetic microsphere and the at least one second anti-cardiac troponin I antibody in solution labeled with fluorescein isothiocyanate.

7. The kit according to claim 1, wherein the components of the diluent are present in the following concentrations: 1 to 10 g/L of the bovine serum albumin, 1 to 50 v/v % of the neonatal bovine serum, 0.1 to 10 v/v % of the goat serum, 0.1 to 10 v/v % of the horse serum, 1 to 11 mmol/L of the dithiothreitol, 1 to 100 mmol/L of the tris (hydroxymethyl) aminomethane, 1 to 100 mmol/L of the hydrated 2-morpholinoethanesulfonic acid, 0.1 to 10 v/v % of the ethylene glycol, 0.1 to 10 v/v % of the glycerol, 0.01 to 2 v/v % of the polysorbate 80, 0.1 to 10 g/L of the casein, and 0.1 to 10 g/L disodium ethylenediaminetetraacetate.

8. The kit according to claim 1, further comprising a low point calibrator and a high point calibrator for cardiac troponin I, and optionally a buffer.

9. The kit according to claim 1, wherein each of the at least one first anti-cardiac troponin I antibody and the at least one second anti-cardiac troponin I antibody in the kit has a concentration of 1-20 µg/mL, the trace marker has a concentration of 5-500 ng/mL, and the magnetic microspheres have a concentration of 0.1-2 mg/mL.

10. A method of preparing the cardiac troponin I ultrasensitive assay kit of claim 1, the method comprising: directly or indirectly labelling the at least one first anti-cardiac troponin I antibody with a trace marker, coating the at least one second anti-cardiac troponin I antibody directly or indirectly on a magnetic microspheres, wherein the at least one first anti-cardiac troponin I antibody to cardiac troponin I and the at least one second anti-cardiac troponin I antibody bind different binding sites of cardiac troponin I; and
preparing the diluent comprising the following components: bovine serum albumin, neonatal bovine serum, goat serum, horse serum, dithiothreitol, tris (hydroxymethyl) aminomethane, hydrated 2-morpholinoethanesulfonic acid, ethylene glycol, glycerol, polysorbate 80, casein, and disodium ethylenediaminetetraacetate.

11. The method according to claim 10, wherein
the indirectly labeling comprises labeling the at least one first anti-cardiac troponin I antibody with a trace marker either by a system of fluorescein isothiocyanate and antiisothiocyanate fluorescein antibody or by a system of streptavidin and biotin; and
the indirectly coating comprises indirectly coating the at least one second anti-cardiac troponin I antibody on the magnetic microspheres either by a system of fluorescein isothiocyanate and anti-isothiocyanate fluorescein antibody or by a system of streptavidin and biotin.

12. The method according to claim 10, wherein the trace marker is N-(4-aminobutyl)-N-ethylisoluminol.

13. The method according to claim 10, wherein the magnetic microspheres are a complex of Fe2O3 or Fe3O4 magnetic nanoparticle with an organic polymeric material, the magnetic microspheres having a particle diameter of 0.1 to 5 µm.

14. The method according to claim 10, wherein the components of the diluent are present in the following concentrations: 1 to 10 g/L of the bovine serum albumin, 1 to 50 v/v % of the neonatal bovine serum, 0.1 to 10 v/v % of the goat serum, 0.1 to 10 v/v % of the horse serum, 1 to 11 mmol/L of the dithiothreitol, 1 to 100 mmol/L of the tris (hydroxymethyl) aminomethane, 1 to 100 mmol/L of the hydrated 2-morpholinoethanesulfonic acid, 0.1 to 10 v/v % of the ethylene glycol, 0.1 to 10 v/v % of the glycerol, 0.01 to 2 v/v % of the polysorbate 80, 0.1 to 10 g/L of the casein, and 0.1 to 10 g/L disodium ethylenediaminetetraacetate.

15. A method for detecting cardiac troponin I, comprising performing a chemiluminescent immunoassay using the kit of claim 1.

* * * * *